(12) United States Patent
Earle et al.

(10) Patent No.: US 6,699,894 B1
(45) Date of Patent: Mar. 2, 2004

(54) METHODS FOR TREATMENT OF INFLAMMATORY BOWEL DISEASE

(75) Inventors: Keith A. Earle, North Wales, PA (US); Hector W. Alila, North Wales, PA (US)

(73) Assignee: OSI Pharmaceuticals, Inc., Melville, NY (US)

( * ) Notice: Subject to any disclaimer, the term of this patent is extended or adjusted under 35 U.S.C. 154(b) by 0 days.

(21) Appl. No.: 10/252,286

(22) Filed: Sep. 23, 2002

Related U.S. Application Data

(63) Continuation of application No. 09/789,848, filed on Feb. 21, 2001, now abandoned.

(51) Int. Cl.[7] .................. A01N 43/40; A01N 43/42; A61K 31/47; A61K 31/57
(52) U.S. Cl. .................. 514/357; 514/307; 514/311; 514/381; 514/382; 514/383; 514/365; 514/394; 514/252.1; 424/400
(58) Field of Search .................. 435/195, 196; 514/357, 522, 252.1, 307, 311, 365, 381, 382, 394, 400, 406, 333, 383, 461, 427; 424/400

(56) References Cited

U.S. PATENT DOCUMENTS 6,066,634 A  *  5/2000  Sperl et al. .................. 514/241

* cited by examiner

*Primary Examiner*—Thurman K. Page
*Assistant Examiner*—Sharmila S Gollamudi
(74) *Attorney, Agent, or Firm*—Shu M. Lee

(57) ABSTRACT

Substituted condensation products of N-benzyl-3-indenylacetamides with heterocyclic aldehydes and other such inhibitors are useful for the treatment of inflammatory bowel disease.

2 Claims, 3 Drawing Sheets

(1 of 3 Drawing Sheet(s) Filed in Color)

METHODS FOR TREATMENT OF INFLAMMATORY BOWEL DISEASE

This application is a continuation under 35 U.S.C. §120 to U.S. patent application Ser. No. 09/789,848, filed Feb. 21, 2001, now abandoned.

TECHNICAL FIELD

This invention relates to the treatment of inflammatory bowel disease.

BACKGROUND OF THE INVENTION

Inflammatory bowel disease ("IBD") refers to two chronic diseases that cause inflammation of the intestines: ulcerative colitis and Crohn's disease. Ulcerative colitis and Crohn's disease are different diseases that manifest similar symptoms. Up to 2,000,000 Americans are estimated to suffer from IBD.

Both diseases are chronic and most frequently have their onset in early adult life. Some patients have alternating periods of remission alternating with periods of relapse or flare. Other patients have continuous symptoms from continued inflammation. The severity of the diseases varies widely between individuals. Some suffer only mild symptoms, but others have severe and disabling symptoms. Medical science has not yet discovered a cause or cure.

The most common symptom of both ulcerative colitis and Crohn's disease is diarrhea, sometimes severe, that may require frequent visits to a toilet—in some cases up to 20 or more times a day. Abdominal cramps often occur, the severity of which may be correlated with the degree of diarrhea present. Blood may also appear in the stools, especially with colitis. Fever, fatigue, and loss of appetite may accompany these symptoms (with consequent weight loss).

At times, some ulcerative colitis and Crohn's disease patients experience constipation during periods of active disease. In Crohn's disease, this can result from a partial obstruction usually of the small intestine. In colitis, constipation is most often a consequence of inflammation of the rectum (also known as proctitis); the colon has a nervous reaction and stasis of stool occurs upstream.

Inflammation can affect gut nerves in such a way as to make the patient feel that there is stool present ready to be evacuated when there actually is none. That results in tenesmus, an uncomfortable urge to defecate but where nothing happens. The feeling of urgency to pass stool also is a frequent consequence of proctitis. Inability to retain stool is an extreme manifestation of urgency.

Pain usually results from intestinal cramping or inflammation causing reflex irritability of the nerves and muscles that control intestinal contractions. Pain may also indicate the presence of severe inflammation or the development of a complication such as an abscess or a perforation of the intestinal wall.

Current IBD drug therapies are inadequate. The two most widely used drug families are steroids and 5-aminosalicylic acid (5-ASA) drugs, both of which reduce inflammation of the affected parts of the intestines. Immunosuppressive drugs such as 6-mercaptopurine are increasingly used for long-term treatment of IBD. They are particularly used for patients dependent on chronic high-dose steroid therapy with its severe and predictable side effects.

Sulfasalazine (Azulfidine, Azulfidine EN-Tabs in the US; SalazopyrinEN-Tabs, SAS in Canada; salazosulfapyridine, salicylazosulfapyridine) is the "staple" drug generally prescribed as the first course of therapy for IBD patients. It is an 5-ASA type drug intended first to reduce inflammation of the intestinal lining and then to maintain remission in mild to moderate cases. Side effects are common and include nausea, heartburn, headache, dizziness, anemia, and skin rashes. It is also known to cause a reduced sperm count in men, but only for the duration of treatment. It may also turn urine a bright orange-yellow color. Hence, there have been considerable efforts to develop alternatives to sulfapyridine (a sulfasalazine metabolite) and other sulfa-based drugs for the treatment of IBD.

Olsalazine is a drug that uses a different mechanism to deliver 5-ASA to the terminal ileum and colon. Whereas sulfasalazine links a 5-ASA molecule with a sulfapyridine molecule, olsalazine links two 5-ASA molecules. This compound passes through the stomach and upper ileum. Intestinal bacteria break the drug in the terminal ileum, making 5-ASA available there and also in the colon. The major side effect is watery diarrhea, seen in many patients. Patients with ulcerative colitis or Crohn's disease affecting the entire colon seem especially susceptible. Increased cramping and audible bowel sounds are also commonly reported.

5-ASA drugs commonly fail. When that happens or when symptoms are more severe, the next therapeutic step usually involves steroids (e.g., prednisone, prednisolone or hydrocortisone) which are very powerful anti-inflammatory drugs. These are available in oral, enema, or suppository forms. The topical forms are useful in treating distal colitis. The oral forms are useful for achieving remission in mild to moderately active ulcerative colitis and Crohn's disease. They are not useful for prolonged use in maintaining a remission. The oral forms can, however, be effective in suppressing active Crohn's disease to the point where it appears to be in remission.

Steroid side effects vary widely between patients, but are generally pretty severe particularly when used at moderate to high doses (e.g., more than 15 mg. prednisone daily). Common side effects include rounding of the face (moon face) and increase in the size of fat pads on the upper back and back of the neck (buffalo hump), acne, increased appetite with consequent weight gain, increased body hair, osteoporosis (especially in women), compression fractures of the vertebrae, diabetes, hypertension, cataracts, increased susceptibility to infections, glaucoma, weakness of arm, leg, shoulder, and pelvic muscles, personality changes including depression (suicidal tendencies are not uncommon), irritability, nervousness, and insomnia. Children's growth may also be affected, even by small doses. An important and serious (but rare) complication of steroid therapy is avascularnecrosis of the hip. This results in death of the bone in the hip joint resulting in arthritis and severe pain.

Long term use of steroids (more than a few days) suppresses the adrenal gland's normal production of steroids and can affect its function for along time (up to a year, or in some cases even two) even after steroid use has stopped. During this period, the body may not be able to produce an adequate supply of steroids during extreme stress, such as surgery or severe infection.

Steroid drugs unfortunately can cause osteoporosis that causes bones to become weak and much more likely to fracture. Without protection within the first six months of steroid therapy, a person can lose 10 percent to 20 percent of bone mass. As many as one in four of these people may eventually suffer a fracture as a result. Unlike osteoporosis associated with aging, steroid-induced osteoporosis can occur at any age, even in children. For many years it was thought that only high (i.e., more than 20 mg. daily) doses of steroids were a problem, more recent studies have shown that chronic use of low oral doses—as little as 7.5 milligrams a day—can cause significant though gradual bone loss.

Immunosuppressives such as 6-mercaptopurine or orazathioprine are increasingly used in treating more severe IBD that does not respond to 5-ASA therapy and short-term steroid therapy. The most frequent use of immunosuppressives is for patients unable to reduce the steroid dosages in steroid-dependent patients without causing a disease flare. The minimum time to respond to immunosuppressives is about three months and can be as long as 12 months. These drugs can be effective in maintaining remission in many patients. An important side effect is pancreatitis. This usually occurs within a few weeks of starting treatment and is manifested by upper abdominal pain that may radiate to the back and be associated with nausea and vomiting. If pancreatitis occurs, then the patient cannot take the drug in the future.

Drug treatments are reportedly ultimately ineffective in about 20% of ulcerative colitis patients. Accordingly, these patients must have their colons removed due to debilitating symptoms. The colon may also removed because of the threat of cancer. Removal of the colon permanently cures the colitis and usually all related symptoms. However, removal of the colon is obviously undesirable because it is disfiguring and causes a loss of bowel control, among other things.

There is no surgical cure for Crohn's disease. Physicians reportedly use the phrases "minimalist surgery" and "surgery avoidance" when discussing surgical options for Crohn's disease. This is because new Crohn's lesions can appear after previously diseased areas have been removed and even diseased tissue may be functionally useful. Many surgeons also feel that surgery in Crohn's patients just leads to more surgery. When surgery is performed for Crohn's disease, it usually involves a resection of the small intestine.

Thus, there is an urgent, unmet need for safe and effective drug therapies for IBD patients.

SUMMARY OF THE INVENTION

This invention represents a novel therapy for treating patients (e.g., humans or companion animals) with IBD without the substantial side effects of prior pharmaceutical approaches. Specifically, this invention involves the administration of an inhibitor of both phosphodiesterase 2 ("PDE2") and phosphodiesterase 5 ("PDE5") to a mammal in need of treatment for IBD. As demonstrated below, both of those enzymes are present in intestinal tissue affected by IBD. In narrower aspects of this invention, this invention involves the administration of compounds of Formula I below to a mammal in need of treatment for IBD.

BRIEF DESCRIPTION OF THE FIGURES

The file of this patent contains at least one drawing executed in color. Copies of this patent with color drawing (s) will be provided by the Patent and Trademark Office upon request and payment of the necessary fee.

DETAILED DESCRIPTION OF THE INVENTION

Figure 1:
FIG. 1 is a photomicrograph (10× magnification) of a small intestine tissue section taken from a dog with IBD prior to therapy with a compound employed in the practice of this invention.

As discussed above, the present invention includes the administration of an inhibitor of both PDE2 and PDE5 to a mammal in need of treatment for IBD. In addition, this invention includes the use of compounds of Formula I below (as well as their pharmaceutically acceptable salts) for treating a mammal with inflammatory bowel disease:

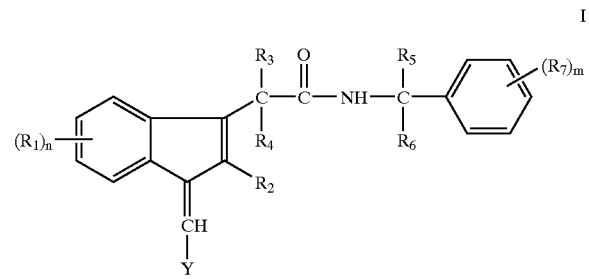

wherein $R_1$ is independently selected in each instance from the group consisting of hydrogen, halogen, lower alkyl, lower alkoxy, amino, lower alkylamino, di-lower alkylamino, lower alkylmercapto, lower alkyl sulfonyl, cyano, carboxamide, carboxylic acid, mercapto, sulfonic acid, xanthate and hydroxy;

$R_2$ is selected from the group consisting of hydrogen and lower alkyl;

$R_3$ is selected from the group consisting of hydrogen, halogen, amino, hydroxy, lower alkyl amino, and di-loweralkylamino;

$R_4$ is hydrogen, or $R_3$ and $R_4$ together are oxygen;

$R_5$ and $R_6$ are independently selected from the group consisting of hydrogen, lower alkyl, hydroxy-substituted lower alkyl, amino lower alkyl, alkylamino-lower alkyl, lower alkyl amino di-lower alkyl, lower alkyl nitrile, —$CO_2H$, —$C(O)NH_2$, and a $C_2$ to $C_6$ amino acid;

$R_7$ is independently selected in each instance from the group consisting of hydrogen, amino lower alkyl, lower alkoxy, lower alkyl, hydroxy, amino, lower alkyl amino, di-lower alkyl amino, halogen, —$CO_2H$, —$SO_3H$, —$SO_2NH_2$, and —$SO_2$(lower alkyl);

m and n are integers from 0 to 3 independently selected from one another;

Y is selected from the group consisting of quinolinyl, isoquinolinyl, pyridinyl, pyrimidinyl, pyrazinyl, imidazolyl, indolyl, benzimidazolyl, triazinyl, tetrazolyl, thiophenyl, furanyl, thiazolyl, pyrazolyl, or pyrrolyl, or subsituted variants thereof wherein the substituents are one or two selected from the group consisting of halogen, lower alkyl, lower alkoxy, amino, lower alkylamino, di-lower alkylamino, hydroxy, —$SO_2$(lower alkyl) and —$SO_2NH_2$.

Preferred compounds of this invention for use with the methods described herein include those of Formula I where:

$R_1$ is selected from the group consisting of halogen, lower alkoxy, amino, hydroxy, lower alkylamino and di-loweralkylamino, preferably halogen, lower alkoxy, amino and hydroxy;

$R_2$ is lower alkyl;

$R_3$ is selected from the group consisting of hydrogen, halogen, hydroxy, amino, lower alkylamino and di-loweralkylamino, preferably, hydrogen, hydroxy and lower alkylamino;

$R_5$ and $R_6$ are independently selected from the group consisting of hydrogen, hydroxy-substituted lower alkyl, amino lower alkyl, lower alkylamino-lower alkyl, lower alkyl amino di-lower alkyl, —$CO_2H$, —$C(O)NH_2$; preferably hydrogen, hydroxy-substituted lower alkyl, lower alkyl amino di-lower alkyl, —$CO_2H$, and —$C(O)NH_2$;

$R_7$ is independently selected in each instance from the group consisting of hydrogen, lower alkoxy, hydroxy, amino, lower alkyl amino, di-lower alkyl amino, halogen, —$CO_2H$, —$SO_3H$, —$SO_2NH_2$, and —$SO_2$(lower alkyl); preferably hydrogen, lower alkoxy, hydroxy, amino, amino lower alkyl, halogen, —$CO_2H$, —$SO_3H$, —$SO_2NH_2$, and —$SO_2$(lower alkyl);

Preferably, at least one of the $R_7$ substituents is para- or ortho-located; most preferably ortho-located;

Y is selected from the group consisting of quinolinyl, isoquinolinyl, pyridinyl, pyrimidinyl and pyrazinyl or said substituted variants thereof.

Preferably, the substituents on Y are one or two selected from the group consisting of lower alkoxy, amino, lower alkylamino, di-lower alkylamino, hydroxy, —$SO_2$(lower alkyl) and —$SO_2NH_2$; most preferably lower alkoxy, di-lower alkylamino, hydroxy, —$SO_2$(lower alkyl) and —$SO_2NH_2$.

The present invention also is a method of treating a mammal with IBD by administering to a patient a pharmacologically effective amount of a pharmaceutical composition that includes a compound of Formula I, wherein $R_1$ through $R_7$ and Y are as defined above. Preferably, this composition is administered without therapeutic amounts of an NSAID.

Compounds of this invention are inhibitors of phosphodiesterases PDE5 and PDE2. For convenience, the PDE inhibitory activity of such compounds can be tested as taught in U.S. patent application Ser. No. 09/046,739 filed Mar. 24, 1998 to Pamukcu et al., which is incorporated herein by reference. Thus, compounds employed in this invention are useful inhibitors of PDE5 and PDE2.

Additional compounds besides those of Formula I can be identified for inhibitory effect on the activity of PDE2 and/or PDE5. Alternatively, cyclic nucleotide levels in whole cells are measured by radioimmunoassay ("RIA") and compared to untreated and drug-treated tissue samples and/or isolated enzymes.

Phosphodiesterase activity can be determined using methods known in the art, such as a method using radioactive $^3H$ cyclic GMP (cGMP)(cyclic 3',5'-guanosine monophosphate) as the substrate for the PDE enzyme. (Thompson, W. J., Teraski, W. L., Epstein, P. M., Strada, S. J., *Advances in Cyclic Nucleotide Research,* 10:69–92, 1979, which is incorporated herein by reference). In brief, a solution of defined substrate $^3H$-cGMP specific activity (0.2 µM; 100,000 cpm; containing 40 mM Tris-HCl (pH 8.0), 5 mM $MgCl_2$ and 1 mg/mL BSA) is mixed with the drug to be tested in a total volume of 400 µl. The mixture is incubated at 30° C. for 10 minutes with isolated PDE2 and/or PDE5. Reactions are terminated, for example, by boiling the reaction mixture for 75 seconds. After cooling on ice, 100 µl of 0.5 mg/mL snake venom (*O. Hannah* venom available from Sigma) is added and incubated for 10 minutes at 30° C. This reaction is then terminated by the addition of an alcohol, e.g. 1 mL of 100% methanol. Assay samples are applied to 1 mL Dowex 1-X8 column; and washed with 1 mL of 100% methanol. The amount of radioactivity in the breakthrough and the wash from the column is combined and measured with a scintillation counter. The degree of phosphodiesterase inhibition is determined by calculating the amount of radioactivity in drug-treated reactions and comparing against a control sample (a reaction mixture lacking the tested compound but with drug solvent).

Alternatively, the ability of desirable compounds to inhibit the phosphodiesterases of this invention is reflected by an increase in cGMP in IBD tissue samples exposed to a compound being evaluated. The amount of PDE activity can be determined by assaying for the amount of cyclic GMP in the extract of treated cells using RIA. When PDE activity is evaluated in this fashion, a combined cGMP hydrolytic activity is assayed. The test compound is then incubated with the tissue at a concentration of compound between about 200 µM to about 200 M. About 24 to 48 hours thereafter, the culture media is removed from the tissue, and the cells are solubilized. The reaction is stopped by using 0.2N HCl/50% MeOH. A sample is removed for protein assay. Cyclic GMP is purified from the acid/alcohol extracts of cells using anion-exchange chromatography, such as a Dowex column. The cGMP is dried, acetylated according to published procedures, such as using acetic anhydride in triethylamine, (Steiner, A. L., Parker, C. W., Kipnis, D. M., *J. Biol. Chem.,* 247(4):1106–13, 1971, which is incorporated herein by reference). The acetylated cGMP is quantitated using radioimmunoassay procedures (Harper, J., Brooker, G., *Advances in Nucleotide Research,* 10:1–33, 1979, which is incorporated herein by reference). Iodinated ligands (tyrosine methyl ester) of derivatized cyclic GMP are incubated with standards or unknowns in the presence of antisera and appropriate buffers. Antiserum may be produced using cyclic nucleotide-haptene directed techniques. The antiserum is from sheep injected with succinyl-cGMP-albumin conjugates and diluted 1/20,000. Dose-interpolation and error analysis from standard curves are applied as described previously (Seibert, A. F., Thompson, W. J., Taylor, A., Wilbourn, W. H., Barnard, J. and Haynes, J., *J. Applied Physiol.,* 72:389–395, 1992, which is incorporated herein by reference).

In addition, the tissue may be acidified, frozen (−70° C.) and also analyzed for cGMP and cAMP.

More specifically as to tissue testing, the PDE inhibitory activity effect of a compound can also be determined from tissue biopsies obtained from humans or tissues from animals exposed to the test compound. A sample of tissue is homogenized in 500 µl of 6% trichloroacetic acid ("TCA"). A known amount of the homogenate is removed for protein analysis. The remaining homogenate is allowed to sit on ice for 20 minutes to allow for the protein to precipitate. Next, the homogenate is centrifuged for 30 minutes at 15,000 g at 4° C. The supernatant is recovered, and the pellet recovered. The supernatant is washed four times with five volumes of water saturated diethyl ether. The upper ether layer is discarded between each wash. The aqueous ether extract is dried in a speed vac. Once dried, the sample can be frozen for future use, or used immediately. The dried extract is dissolved in 500 µl of assay buffer. The amount of PDE inhibition is determined by assaying for the amount of cyclic nucleotides using RIA procedures as described above.

In addition to compounds disclosed herein, other compounds that inhibit both PDE2 and PDE5 include compounds disclosed in U.S. Pat. No. 5,401,774 (e.g., exisulind), U.S. Pat. Nos. 6,063,818, 5,998,477, and 5,965,619. These patents are incorporated herein by reference.

When referring to an "a physiologically effective amount of an inhibitor of PDE2 and PDE5" we mean not only a single compound that inhibits those enzymes but a combination of several compounds, each of which can inhibit one or both of those enzymes. Single compounds that inhibit both enzymes are preferred.

As used herein, the term "halo" or "halogen" refers to chloro, bromo, fluoro and iodo groups, and the term "alkyl" refers to straight, branched or cyclic alkyl groups and to substituted aryl alkyl groups. The term "lower alkyl" refers to $C_1$ to $C_8$ alkyl groups.

The term "hydroxy-substituted lower alkyl" refers to lower alkyl groups that are substituted with at least one hydroxy group, preferably no more than three hydroxy groups.

The term "—$SO_2$(lower alkyl)" refers to a sulfonyl group that is substituted with a lower alkyl group.

The term "lower alkoxy" refers to alkoxy groups having from 1 to 8 carbons, including straight, branched or cyclic arrangements.

The term "lower alkylmercapto" refers to a sulfide group that is substituted with a lower alkyl group; and the term "lower alkyl sulfonyl" refers to a sulfone group that is substituted with a lower alkyl group.

The term "pharmaceutically acceptable salt" refers to non-toxic acid addition salts and alkaline earth metal salts of the compounds of Formula I. The salts can be prepared in situ during the final isolation and purification of such compounds, or separately by reacting the free base or acid functions with a suitable organic acid or base, for example. Representative acid addition salts include the hydrochloride, hydrobromide, sulfate, bisulfate, acetate, valerate, oleate, palmatate, stearate, laurate, borate, benzoate, lactate, phosphate, tosylate, mesylate, citrate, maleate, fumarate, succinate, tartrate, glucoheptonate, lactobionate, lauryl sulfate salts and the like. Representative alkali and alkaline earth metal salts include the sodium, calcium, potassium and magnesium salts.

It will be appreciated that certain compounds of Formula I can possess an asymmetric carbon atom and are thus capable of existing as enantiomers. Unless otherwise specified, this invention includes such enantiomers, including any racemates. The separate enaniomers may be synthesized from chiral starting materials, or the racemates can be resolved by conventional procedures that are well known in the art of chemistry such as chiral chromatography, fractional cyrstallization of diastereomeric salts and the like.

Compounds of Formula I also can exist as geometrical isomers (Z and E); the Z isomer is preferred.

Compounds of this invention may be formulated into pharmaceutical compositions together with pharmaceutically acceptable carriers for oral administration in solid or liquid form, or for rectal or topical administration, although carriers for oral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers include liquid dosage forms for oral administration, e.g., pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for topical administration include DMSO, alcohol or propylene glycol and the like that can be employed with patches or other liquid-retaining material to hold the medicament in place on the skin so that the medicament will not dry out.

Pharmaceutically acceptable carriers for rectal administration are preferably suppositories that may contain, in addition to the compounds of this invention excipients such as cocoa butter or a suppository wax, or gel.

The pharmaceutically acceptable carrier and compounds of this invention are formulated into unit dosage forms for administration to a patient. The dosage levels of active ingredient (i.e., compounds of this invention) in the unit dosage may be varied so as to obtain an amount of active ingredient effective to achieve lesion-eliminating activity in accordance with the desired method of administration (i.e., oral or rectal). The selected dosage level therefore depends upon the nature of the active compound administered, the route of administration, the desired duration of treatment, and other factors. If desired, the unit dosage may be such that the daily requirement for active compound is in one dose, or divided among multiple doses for administration, e.g., two to four times per day.

The compounds of this invention can be formulated with pharmaceutically acceptable carriers into unit dosage forms in a conventional manner so that the patient in need of therapy for IBD can periodically (e.g., once or more per day) take a compound according to the methods of this invention. The exact initial dose of the compounds of this invention can be determined with reasonable experimentation. The initial dosage calculation would also take into consideration several factors, such as the formulation and mode of administration, e.g. oral or intravenous, of the particular compound. A total daily oral dosage of about 50 mg–2.0 gr of such compounds would achieve a desired systemic circulatory concentration. As discussed below, an oral dose of about 800 mg/day has been found appropriate in mammals.

The pharmaceutical compositions of this invention are preferably packaged in a container (e.g., a box or bottle, or both) with suitable printed material (e.g., a package insert)

containing indications and directions for use in the treatment of IBD, etc.

There are several general schemes for producing compounds of Formula I useful in this invention. One general scheme (which has several sub-variations) involves the case where both $R_3$ and $R_4$ are both hydrogen. This first scheme is described immediately below in Scheme I. The other general scheme (which also has several sub-variations) involves the case where at least one of $R_3$ and $R_4$ is a moiety other than hydrogen but within the scope of Formula I above. This second scheme is described below as "Scheme II."

The general scheme for preparing compounds where both $R_3$ and $R_4$ are both hydrogen is illustrated in Scheme I, which is described in part in U.S. Pat. No. 3,312,730, which is incorporated herein by reference. In Scheme I, $R_1$ is as defined in Formula I above. However, in Scheme I, that substituent can also be a reactive moiety (e.g. a nitro group) that later can be reacted to make a large number of other substituted indenes from the nitro-substituted indenes.

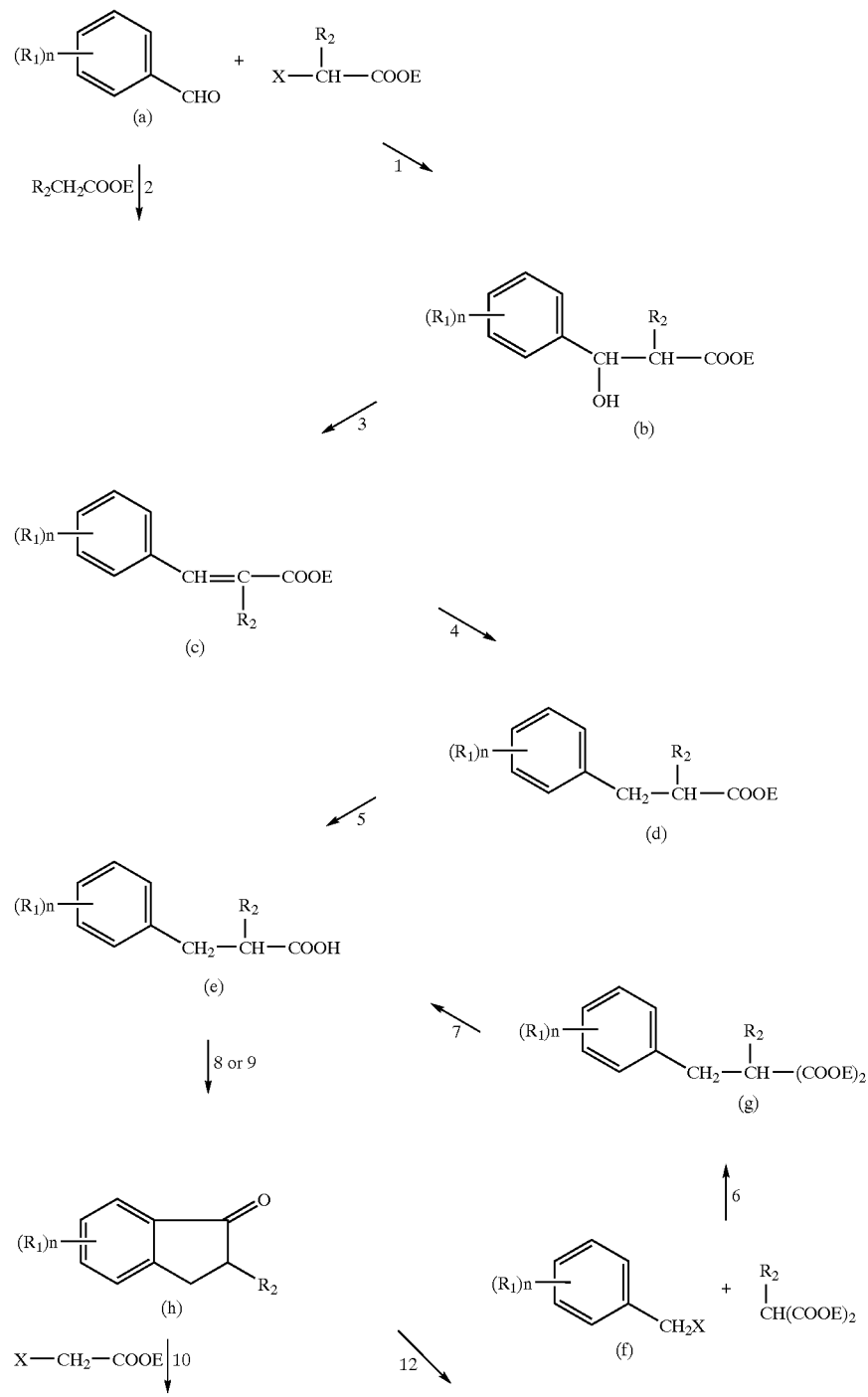

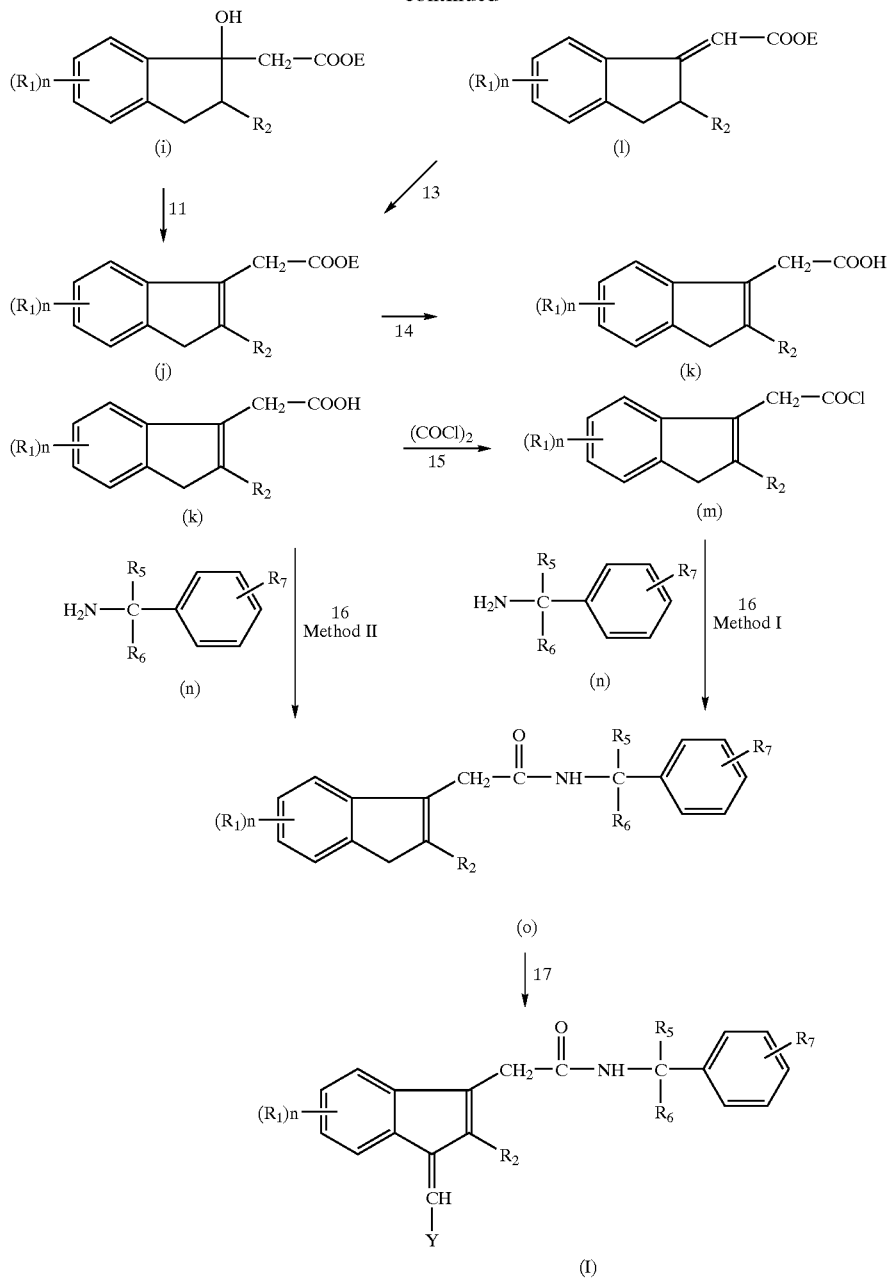

In Scheme I, several sub-variations can be used. In one sub-variation, a substituted benzaldehyde (a) may be condensed with a substituted acetic ester in a Knoevenagel reaction (see reaction 2) or with an α-halogeno propionic ester in a Reformatsky Reaction (see reactions 1 and 3). The resulting unsaturated ester (c) is hydrogenated and hydrolyzed to give a substituted benzyl propionic acid (e) (see reactions 4 and 5). Alternatively, a substituted malonic ester in a typical malonic ester synthesis (see reactions 6 and 7) and hydrolysis decarboxylation of the resulting substituted ester (g) yields the benzyl propionic acid (e) directly. This latter method is especially preferable for nitro and alkylthio substituents on the benzene ring.

The next step is the ring closure of the β-aryl proponic acid (e) to form an indanone (h) which may be carried out by a Friedel-Crafts Reaction using a Lewis acid catalyst (Cf. Organic Reactions, Vol. 2, p. 130) or by heating with polyphosphoric acid (see reactions 8 and 9, respectively). The indanone (h) may be condensed with an α-halo ester in the Reformatsky Reaction to introduce the aliphatic acid side chain by replacing the carboxyl group (see reaction 10). Alternately, this introduction can be carried out by the use of a Wittig Reaction in which the reagent is a α-triphenylphosphinyl ester, a reagent that replaces the carbonyl with a double bond to the carbon (see reaction 12). This product (1) is then immediately rearranged into the indene (j)(see reaction 13). If the Reformatsky Reaction route is used, the intermediate 3-hydroxy-3-aliphatic acid derivative i must be dehydrated to the indene (j) (see reaction 11).

The indenylacetic acid (k) in THF then is allowed to react with oxalyl or thionyl chloride or similar reagent to produce the acid chloride (m) (see reaction 15), whereupon the solvent is evaporated. There are two methods to carry out reaction 16, which is the addition of the benzylamine side chain (n).

Method (I)

In the first method, the benzylamine (n) is added slowly at room temperature to a solution of 5-fluoro-2-methyl-3-indenylacetyl chloride in $CH_2Cl_2$. The reaction mixture is refluxed overnight, and extracted with aqueous HCl (10%), water, and aqueous $NaHCO_3$ (5%). The organic phase is dried ($Na_2SO_4$) and is evaporated to give the amide compound (o).

Method (II)

In the second method, the indenylacetic acid (k) in DMA is allowed to react with a carbodiimide (e.g. N-(3-dimethylaminopropyl)-N'-ethylcarbodiimide hydrochloride) and benzylamine at room temperature for two days. The reaction mixture is added dropwise to stirred ice water. A yellow precipitate is filtered off, is washed with water, and is dried in vacuo. Recrystallization gives the amide compound (o).

Compounds of the type a' (Scheme III), o (Scheme I), t (Scheme II), y (Scheme IIB) may all be used in the condensation reaction shown in Scheme III.

Substituents

X=halogen, usually Cl or Br.

E=methyl, ethyl or benzyl, or lower acyl.

$R_1$, $R_2$, $R_6$, $R_5$, and $R_7$=as defined in Formula I.

Y, n and m=as defined in Formula I.

Reagents and general conditions for Scheme I (numbers refer to the numbered reactions):

(1) Zn dust in anhydrous inert solvent such as benzene and ether.
(2) $KHSO_4$ or p-toluene sulfonic acid.
(3) $NaOC_2H_5$ in anhydrous ethanol at room temperature.
(4) $H_2$ palladium on charcoal, 40 p.s.i. room temperature.
(5) NaOH in aqueous alcohol at 20–100°.
(6) $NaOC_2H_5$ or any other strong base such as NaH or K-t-butoxide.
(7) Acid.
(8) Friedel-Crafts Reaction using a Lewis Acid catalyst Cf. Organic Reactions, Vol. II, p. 130.
(9) Heat with polyphosphoric acid.
(10) Reformatsky Reaction: Zn in inert solvent, heat.
(11) p-Toluene sulfonic acid and $CaCl_2$ or $I_2$ at 200°
(12) Wittig Reaction using $(C_6H_5)_3$ P=C—COOE 20–80° in ether or benzene
(13)
   (a) $NBS/CCl_4$/benzoyl peroxide
   (b) $PtO_2/H_2$ (1 atm.)/acetic acid
(14)
   (a) NaOH
   (b) HCl
(15) Oxalyl or thionyl chloride in $CH_2Cl_2$ or THF
(16)
   Method I: 2 equivalents of $NH_2$—$C(R_5R_6)$-Ph-$(R_7)_m$
   Method II: carbodiimide in THF
(17) 1N $NaOCH_3$ in MeOH under reflux conditions Indanones within the scope of compound (h) in Scheme I are known in the literature and are thus readily available as intermediates for the remainder of the synthesis so that reactions 1–7 can be conveniently avoided. Among such known indanones are:

5-methoxyindanone
6-methoxyindanone
5-methylindanone
5-methyl-6-methoxyindanone
5-methyl-7-chloroindanone
4-methoxy-7-chloroindanone
4-isopropyl-2,7-dimethylindanone
5,6,7-trichloroindanone
2-n-butylindanone
5-methylthioindanone Scheme II has two mutually exclusive sub-schemes: Scheme IIA and Scheme II B. Scheme II A is used when $R_3$ is hydroxy and $R_4$ is hydrogen or when the two substituents form an oxo group. When $R_3$ is lower alkyl amino, Scheme II B is employed.

Scheme IIA

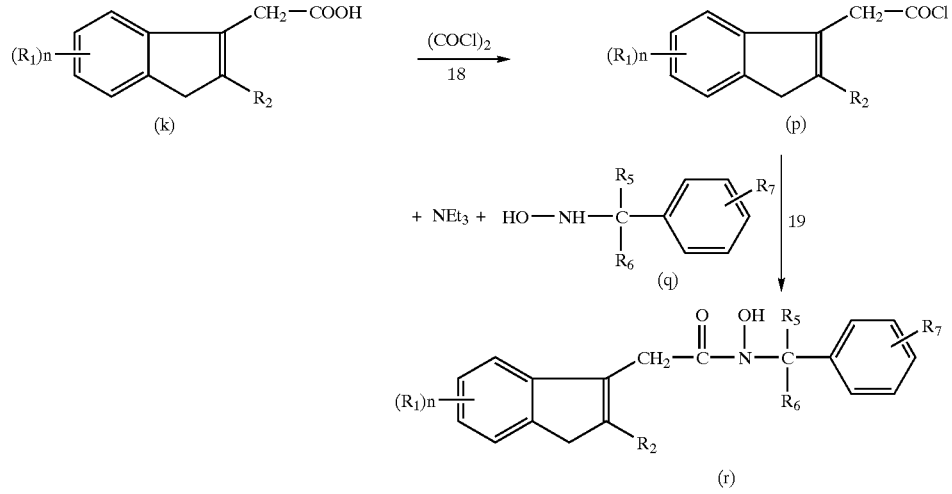

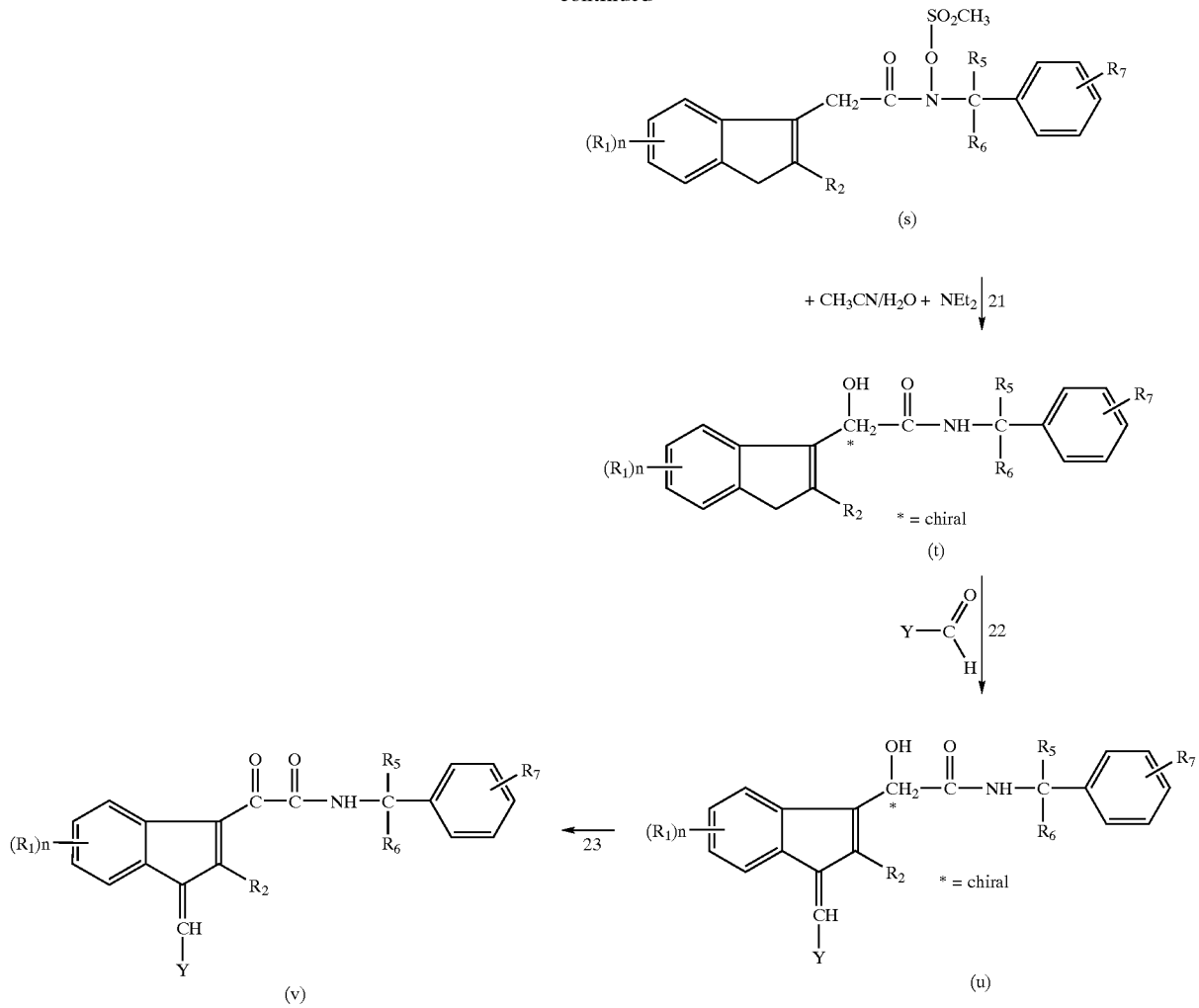

Similar to Scheme I, in Scheme IIA the indenylacetic acid (k) in THF is allowed to react with oxalylchloride under reflux conditions to produce the acid chloride (p) (see reaction 18), whereupon the solvent is evaporated. In reaction 19, a 0° C. mixture of a benzyl hydroxylamine hydrochloride (q) and Et$_3$N is treated with a cold solution of the acid chloride in CH$_2$Cl$_2$ over a period of 45–60 minutes. The mixture is warmed to room temperature and stirred for one hour, and is treated with water. The resulting organic layer is washed with 1 N HCl and brine, is dried over magnesium sulfate and is evaporated. The crude product, a N-hydroxy-N-benzyl acetamide (r) is purified by crystallization or flash chromatography. This general procedure is taught by Hoffman et al., JOC 1992, 57, 5700–5707.

The next step is the preparation of the N-mesyloxy amide (s) in reaction 20, which is also taught by Hoffman et al., JOC 1992, 57, 5700–5707. Specifically, to a solution of the hydroxamic acid (r) in CH$_2$Cl$_2$ at 0° C. is added triethylamine. The mixture is stirred for 10–12 minutes, and methanesulfonyl chloride is added dropwise. The mixture is stirred at 0° C. for two hours, is allowed to warm to room temperature, and is stirred for another two hours. The organic layer is washed with water, 1 N HCl, and brine, and is dried over magnesium sulfate. After rotary evaporation, the product(s) is usually purified by crystallization or flash chromatography.

The preparation of the N-benzyl-α-(hydroxy) amide (t) in reaction 21, is also taught by Hoffman et al., JOC 1992, 57, 5700–5707 and Hoffman et al., JOC 1995, 60, 4121–4125. Specifically, to a solution of the N-(mesyloxy) amide(s) in CH$_3$CN/H$_2$O is added triethylamine in CH$_3$CN over a period of 6–12 hours. The mixture is stirred overnight. The solvent is removed, and the residue is dissolved in ethyl acetate. The solution is washed with water, 1 N HCl, and brine, and is dried over magnesium sulfate. After rotary evaporation, the product (t) is usually purified by recrystallization.

Reaction 22 in Scheme IIA involves a condensation with certain aldehydes, which is described in Scheme III below, a scheme that is common to products made in accordance with Schemes I, IIA and IIB.

The final reaction 23 in Scheme IIA is the preparation of the N-benzyl-α-ketoamide (v), which involves the oxidation of a secondary alcohol (u) to a ketone by e.g., a Pfitzner-Moffatt oxidation, which selectively oxidizes the alcohol without oxidizing the Y group. Compounds (u) and (v) may be derivatized to obtain Scheme IIB

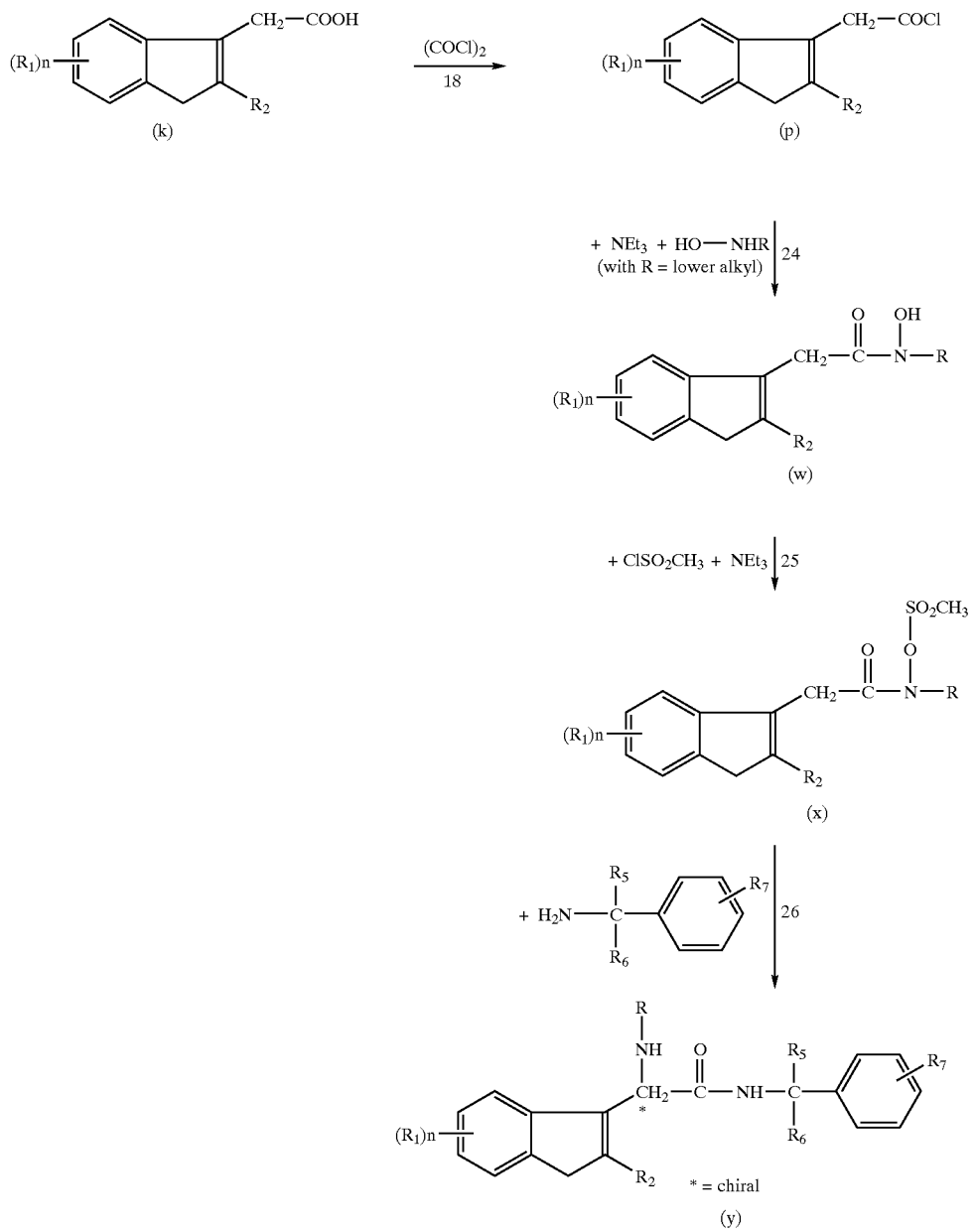

compounds with $R_3$ and $R_4$ groups as set forth in Formula I.

As explained above, Scheme IIB is employed when $R_3$ is lower alkyl amino. Similar to Scheme I, in Scheme IIB the indenylacetic acid (k) in THF is allowed to react with oxalylchloride under reflux conditions to produce the acid chloride (p) (see reaction 18), whereupon the solvent is evaporated. In reaction 24, a mixture of an alkyl hydroxylamine hydrochloride (i.e. HO-NHR where R is a lower alkyl, preferably isopropyl) and $Et_3N$ is treated at 0° C. with a cold solution of the acid chloride in $CH_2Cl_2$ over a period of 45–60 minutes. The mixture is warmed to room temperature and is stirred for one hour, and is diluted with water. The resulting organic layer is washed with 1 N HCl and brine, is dried over magnesium sulfate and is evaporated. The crude product, a N-hydroxy-N-alkyl acetamide (w) is purified by crystallization or flash chromatography. This general procedure is also taught by Hoffman et al., JOC 1992, 57, 5700–5707.

The preparation of the N-mesyloxy amide (x) in reaction 25, which is also taught by Hoffman et al., JOC 1992, 57, 5700–5707. Specifically, a solution of the hydroxamic acid (w) in $CH_2Cl_2$ at 0° C. is treated with triethylamine, is stirred for 10–12 minutes, and is treated dropwise with methanesulfonyl chloride. The mixture is stirred at 0° C. for two hours, is allowed to warm to room temperature, and is stirred for another two hours. The resulting organic layer is washed with water, 1 N HCl, and brine, and is dried over magnesium sulfate. After rotary evaporation, the product (x) is usually purified by crystallization or flash chromatography.

The preparation of the N-benzyl indenyl-α-loweralkylamino-acetamide compound (y) in Scheme IIB as taught by Hoffman et al., JOC 1995, 60, 4121–25 and J. Am. Chem Soc. 1993, 115, 5031–34, involves the reaction of the N-mesyloxy amide (x), with a benzylamine in $CH_2Cl_2$ at 0° C. is added over a period of 30 minutes. The resulting solution is stirred at 0° C. for one hour and at room temperature overnight. The solvent is removed, and the residue is treated with 1 N NaOH. The extract with $CH_2Cl_2$ is washed with water and is dried over magnesium sulfate. After rotary evaporation, the product (y) is purified by flash chromatography or crystallization.

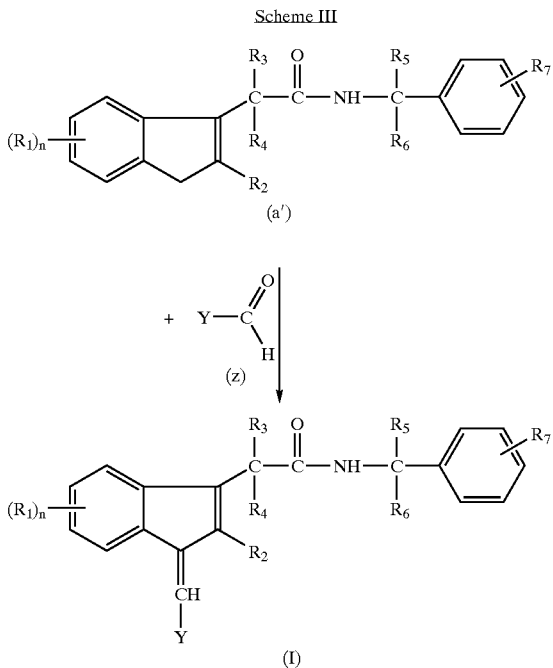

Scheme III involves the condensation of the heterocycloaldehydes (i.e., Y-CHO) with the indenyl amides to produce the final compounds of Formula I. This condensation is employed, for example, in reaction 17 in Scheme I above and in reaction 22 in Scheme IIA. It is also used to convert compound (y) in Scheme IIB to final compounds of Formula I.

In Scheme III, the amide (a') from the above schemes, an N-heterocycloaldehyde (z), and sodium methoxide (1 M in methanol) are stirred at 60° C. under nitrogen for 24 hours. After cooling, the reaction mixture is poured into ice water. A solid is filtered off, is washed with water, and is dried in vacuo. Recrystallization provides a compound of Formula I in Schemes I and IIB and the intermediate (u) in Scheme IIA.

As has been pointed out above, it is preferable in the preparation of many types of the compounds of this invention, to use a nitro substituent on the benzene ring of the indanone nucleus and convert it later to a desired substituent since by this route a great many substituents can be reached. This is done by reduction of the nitro to the amino group followed by use of the Sandmeyer reaction to introduce chlorine, bromine, cyano or xanthate in place of the amino. From the cyano derivatives, hydrolysis yields the carboxamide and carboxylic acid; other derivatives of the carboxy group such as the esters can then be prepared. The xanthates, by hydrolysis, yield the mercapto group that may be oxidized readily to the sulfonic acid or alkylated to an alkylthio group that can then be oxidized to alkylsulfonyl groups. These reactions may be carried out either before or after the introduction of the 1-substituent.

The foregoing may be better understood from the following examples that are presented for purposes of illustration and are not intended to limit the scope of the invention. As used in the following examples, the references to substituents such as $R_1$, $R_2$, etc., refer to the corresponding compounds and substituents in Formula I above.

EXAMPLE 1

(Z)-5-Fluoro-2-Methyl-(4-Pyridinylidene)-3-(N-Benzyl)-Indenylacetamide (A) p-Fluoro-α-methylcinnamic acid p-Fluorobenzaldehyde (200 g, 1.61 mol), propionic anhydride (3.5 g, 2.42 mol) and sodium propionate (155 g, 1.61 mol) are mixed in a one liter three-necked flask which had been flushed with nitrogen. The flask is heated gradually in an oil-bath to 140° C. After 20 hours, the flask is cooled to 100° C. and poured into 8 l of water. The precipitate is dissolved by adding potassium hydroxide (302 g) in 2 l of water. The aqueous solution is extracted with ether, and the ether extracts are washed with potassium hydroxide solution. The combined aqueous layers are filtered, are acidified with concentrated HCl, and are filtered. The collected solid, p-fluoro-α-methylcinnamic acid, is washed with water, and is dried and used as obtained.

(B) p-Fluoro-α-methylhydrocinnamic acid

To p-fluoro-α-methylcinnamic acid (177.9 g, 0.987 mol) in 3.6 l ethanol is added 11.0 g of 5% Pd/C. The mixture is reduced at room temperature under a hydrogen pressure of 40 p.s.i. When hydrogen uptake ceases, the catalyst is filtered off, and the solvent is evaporated in vacuo to give the product, p-fluoro-α-methylhydrocinnamic acid, which was used directly in the next step.

(C) 6-Fluoro-2-methylindanone

To 932 g polyphosphoric acid at 70° C. (steam bath) is added p-fluoro-α-methylhydrocinnamic acid (93.2 g, 0.5 mol) slowly with stirring. The temperature is gradually raised to 95° C., and the mixture is kept at this temperature for 1 hour. The mixture is allowed to cool and is added to 2 l. of water. The aqueous suspension is extracted with ether. The extract is washed twice with saturated sodium chloride solution, 5% $Na_2CO_3$ solution, and water, and is dried, and is concentrated on 200 g silica-gel; the slurry is added to a five pound silica-gel column packed with 5% etherpetroleum ether. The column is eluted with 5–10% etherpetroleum ether, to give 6-fluoro-2-methylindanone. Elution is followed by TLC.

(D) 5-fluoro-2-methylindenyl-3-acetic acid

A mixture of 6-fluoro-2-methylindanone (18.4 g, 0.112 mol), cyanoacetic acid (10.5 g, 0.123 mol), acetic acid (6.6 g), and ammonium acetate (1.7 g) in dry toluene (15.5 ml) is refluxed with stirring for 21 hours, as the liberated water is collected in a Dean Stark trap. The toluene is evaporated, and the residue is dissolved in 60 ml of hot ethanol and 14 ml of 2.2 N aqueous potassium hydroxide solution. 22 g of 85% KOH in 150 ml of water is added, and the mixture refluxed for 13 hours under nitrogen. The ethanol is removed under vacuum, and 500 ml water is added. The aqueous solution is extracted well with ether, and is then boiled with charcoal. The aqueous filtrate is acidified to pH 2 with 50% cold hydrochloric acid. The precipitate is dried and 5-fluoro-2-methylindenyl-3-acetic acid (M.P. 164–166° C.) is obtained.

(E) 5-fluoro-2-methylindenyl-3-acetyl chloride 5-fluoro-2-methylindenyl-3-acetic acid (70 mmol) in THF (70 ml) is allowed to react with oxalylchloride (2 M in $CH_2Cl_2$; 35 ml; 70 mmol) under reflux conditions (24 hours). The solvent is evaporated to yield the title compound, which is used as such in the next step.

(F) 5-Fluoro-2-methyl-3-(N-benzyl)-indenylacetamide

Benzylamine (5 mmol) is added slowly at room temperature to a solution of 5-fluoro-2-methylindenyl-3-acetyl chloride (2.5 mmol.) in $CH_2Cl_2$ (10 ml). The reaction mixture is refluxed overnight, and is extracted with aqueous HCl (10%), water, and aqueous $NaHCO_3$ (5%). The organic phase is dried ($Na_2SO_4$) and is evaporated to give the title compound, which is recrystallized from $CH_2Cl_2$ to give the title compound as a white solid (m.p. 144° C.).

(G) (Z)-5-Fluoro-2-methyl-(4-pyridinylidene)-3-(N-benzyl)-indenylacetamide 5-fluoro-2-methyl-3-(N-benzyl)-indenylacetamide (3.38 mmol), 4-pyridinecarboxaldehyde (4 mmol), sodium methoxide (1M $NaOCH_3$ in methanol (30 ml)) are heated at 60° C. under nitrogen with stirring for 24 hours. After cooling, the reaction mixture is poured into ice water (200 ml). A solid is filtered off, washed with water, and dried in vacuo. Recrystallization from $CH_3CN$ gives the title compound (m.p. 202° C.) as a yellow solid ($R_1$=F, $R_2$=$CH_3$, $R_3$=H, $R_4$=H, $R_5$=H, $R_6$=H, $R_7$=H, n=1, m=1, Y=4-pyridinyl).

(H) (E)-5-Fluoro-2-methyl-(4-pyridinylidene)-3-(N-benzyl)-indenylacetamide

The mother liquor obtained from the $CH_3CN$ recrystallization of 1 G is rich on the geometrical isomer of 1 G. The E-isomer can be obtained pure by repeated recrystallizations from $CH_3CN$.

EXAMPLE 2

(Z)-5-Fluoro-2-Methyl-(3-Pyridinylidene)-3-(N-Benzyl)-Indenylacetamide

This compound is obtained from 5-fluoro-2-methyl-3-(N-benzyl)-indenylacetamide (Example 1F) using the procedure of Example 1, part G and replacing 4-pyridinecarboxaldehyde with 3-pyridinecarboxaldehyde. Recrystallization from $CH_3CN$ gives the title compound (m.p. 175° C.)($R_1$=F, $R_2$=$CH_3$, $R_3$=H, $R_4$=H, $R_5$=H, $R_6$=H, $R_7$=H, n=1, m=1, Y=3-pyridinyl).

EXAMPLE 3

(Z)-5-Fluoro-2-Methyl-(2-Pyridinylidene)-3-(N-Benzyl)-Indenylacetamide

This compound is obtained from 5-fluoro-2-methyl-3-(N-benzyl)-indenylacetamide (Example 1F) using the procedure of Example 1, part G and replacing 4-pyridinecarboxaldehyde with 2-pyridinecarboxaldehyde. Recrystallization from ethylacetate gives the title compound (m.p. 218° C.)($R_1$=F, $R_2$=$CH_3$, $R_3$=H, $R_4$=H, $R_5$=H, $R_6$=H, $R_7$=H, n=1, m=1, Y=2-pyridinyl).

EXAMPLE 4

(Z)-5-Fluoro-2-Methyl-(4-Quinolinylidene)-3-(N-Benzyl)-Indenylacetamide

This compound is obtained from 5-fluoro-2-methyl-3-(N-benzyl)-indenylacetamide (Example 1F) using the procedure of Example 1, part G and replacing 4-pyridinecarboxaldehyde with 4-quinolinecarboxaldehyde. Recrystallization from ethylacetate gives the title compound (m.p. 239° C.)($R_1$=F, $R_2$=$CH_3$, $R_3$=H, $R_4$=H, $R_5$=H, $R_6$=H, $R_7$=H, n=1, m=1, Y=4-quinolinyl).

EXAMPLE 5

(Z)-5-Fluoro-2-Methyl-(4,6-Dimethyl-2-Pyridinylidene)-3-(N-Benzyl)-Indenylacetamide 5-Fluoro-2-methyl-3-(N-benzyl)-indenylacetamide from Example 1, part F is allowed to react with 4,6-dimethyl-2-pyridinecarboxaldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=4,6-dimethyl-2-pyridinyl).

EXAMPLE 6

(Z)-5-Fluoro-2-Methyl-(3-Quinolinylidene)-3-(N-Benzyl)-Indenylacetamide

5-Fluoro-2-methyl-3-(N-benzyl)-indenylacetamide from Example 1, part F is allowed to react with 3-quinolinecarboxaldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=3-quinolinyl)

EXAMPLE 7

(Z)-5-Fluoro-2-Methyl-(2-Quinolinylidene)-3-(N-Benzyl)-Indenylacetamide

5-Fluoro-2-methyl-3-(N-benzyl)-indenylacetamide from Example 1, part F is allowed to react with 2-quinolinecarboxaldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=2-quinolinyl).

EXAMPLE 8

(Z)-5-Fluoro-2-Methyl-(Pyrazinylidene)-3-(N-Benzyl)-Indenylacetamide

5-Fluoro-2-methyl-3-(N-benzyl)-indenylacetamide from Example 1, part F is allowed to react with pyrazinealdehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=pyrazinyl).

EXAMPLE 9

(Z)-5-Fluoro-2-Methyl-(3-Pyridazinylidene)-3-(N-Benzyl)-Indenylacetamide

5-Fluoro-2-methyl-3-(N-benzyl)-indenylacetamide from Example 1, part F is allowed to react with pyridazine-3-aldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=3-pyridazinyl).

EXAMPLE 10

(Z)-5-Fluoro-2-Methyl-(4-Pyrimidinylidene)-3-(N-Benzyl)-Indenylacetamide

5-Fluoro-2-methyl-3-(N-benzyl)-indenylacetamide from Example 1, part F is allowed to react with pyrimidine-4-aldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=4-pyrimidinyl).

EXAMPLE 11

(Z)-5-Fluoro-2-Methyl-(2-Methyl-4-Pyrimidinylidene)-3-(N-Benzyl)-Indenylacetamide 5-Fluoro-2-methyl-3-(N-benzyl)-indenylacetamide from Example 1, part F is allowed to react with 2-methyl-pyrimidine-4-aldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=2-methyl-4-pyrimidinyl).

EXAMPLE 12

(Z)-5-Fluoro-2-Methyl-(4-Pyridazinylidene)-3-(N-Benzyl)-Indenylacetamide

5-Fluoro-2-methyl-3-(N-benzyl)-indenylacetamide from Example 1, part F is allowed to react with pyridazine-4-aldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=4-pyridazinyl).

EXAMPLE 13

(Z)-5-Fluoro-2-Methyl-(1-Methyl-3-Indolylidene)-3-(N-Benzyl)-Indenylacetamide

5-Fluoro-2-methyl-3-(N-benzyl)-indenylacetamide from Example 1, part F is allowed to react with 1-methylindole-3-carboxaldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=1-methyl-3-indolyl).

EXAMPLE 14

(Z)-5-Fluoro-2-Methyl-(1-Acetyl-3-Indolylidene)-3-(N-Benzyl)-Indenylacetamide

5-Fluoro-2-methyl-3-(N-benzyl)-indenylacetamide from Example 1, part F is allowed to react with 1-acetyl-3-indolecarboxaldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=H, n=1, m=1, Y=1-acetyl-3-indolyl).

EXAMPLE 15

(Z)-5-Fluoro-2-Methyl-(4-Pyidinylidene)-3-(N-2-Fluorobenzyl)-Indenylacetamide (A) 5-Fluoro-2-methyl-3-(N-2-fluorobenzyl)-indenylacetamide This compound is obtained from 5-fluoro-2-methylindenyl-3-acetyl chloride (Example 1E) using the procedure of Example 1, Part F and replacing benzylamine with 2-fluorobenzylamine.

(B) (Z)-5-Fluoro-2-methyl-(4-pyridinylidene)-3-(N-2-fluorobenzyl)-indenylacetamide 5-Fluoro-2-methyl-3-(N-2-fluorobenzyl)-indenylacetamide is allowed to react with 4-pryidinecarboxaldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=F, n=1, m=1, Y=4-pyridinyl).

EXAMPLE 16

(Z)-5-Fluoro-2-Methyl-(3-Pyridinylidene)-3-(N-2-Fluorobenzyl)-Indenylacetamide

5-Fluoro-2-methyl-3-(N-2-fluorobenzyl)-indenylacetamide from Example 15, part A is allowed to react with 3-pryidinecarboxaldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=F, n=1, m=1, Y=3-pyridinyl).

EXAMPLE 17

(Z)-5-Fluoro-2-Methyl-(2-Pyridinylidene)-3-(N-2-Fluorobenzyl)-Indenylacetamide

5-Fluoro-2-methyl-3-(N-2-fluorobenzyl)-indenylacetamide from Example 15, part A is allowed to react with 2-pyridinecarboxaldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=F, n=1, m=1, Y=2-pyridinyl).

EXAMPLE 18

(Z)-5-Fluoro-2-Methyl-(4-Quinolinylidene)-3-(N-2-Fluorobenzyl)-Indenylacetamide

5-Fluoro-2-methyl-3-(N-2-fluorobenzyl)-indenylacetamide from Example 15, part A is allowed to react with 4-quinolinecarboxaldehyde according to the procedure of Example 1, part G in order to obtain the title compound. Recrystallization gives the title compound ($R_1$=F, $R_2$=$CH_3$, $R_3$=H, $R_4$=H, $R_5$=H, $R_6$=H, $R_7$=F, n=1, m=1, Y=3-quinolinyl).

EXAMPLE 19

(Z)-5-Fluoro-2-Methyl-(3-Pyrazinylidene)-3-(N-2-Fluorobenzyl)-Indenylacetamide

5-Fluoro-2-methyl-3-(N-2-fluorobenzyl)-indenylacetamide from Example 15, part A is allowed to react with pyrazinealdehyde according to the procedure of Example 1, Part G in order to obtain the title compound. Recrystallization gives the title compound ($R_1$=F, $R_2$=$CH_3$, $R_3$=H, $R_4$=H, $R_5$=H, $R_6$=H, $R_7$=F, n=1, m=1, Y=3-pyrazinyl).

EXAMPLE 20

(Z)-5-Fluoro-2-Methyl-(3-Pyridazinylidene)-3-(N-2-Fluorobenzyl)-Indenylacetamide 5-Fluoro-2-methyl-3-(N-2-fluorobenzyl)-indenylacetamide from Example 15, part A is allowed to react with 3-pryidaziine-3-aldehyde according to the procedure of Example 1, Part G in order to obtain the title compound. Recrystallization gives the title compound ($R_1$=F, $R_2$=$CH_3$, $R_3$=H, $R_4$=H, $R_5$=H, $R_6$=H, $R_7$=F, n=1, m=1, Y=3-pyridazinyl).

EXAMPLE 21

(Z)-5-Fluoro-2-Methyl-(3-Pyrimidinylidene)-3-(N-2-Fluorobenzyl)-Indenylacetamide 5-Fluoro-2-methyl-3-(N-2-fluorobenzyl)-indenylacetamide from Example 15, part A is allowed to react with pryimidine-4-aldehyde according to the procedure of Example 1, Part G in order to obtain the title compound. Recrystallization gives the title compound ($R_1$=F, $R_2$=$CH_3$, $R_3$=H, $R_4$=H, $R_5$=H, $R_6$=H, $R_7$=F, n=1, m=1, Y=3-pyrimidinyl).

EXAMPLE 22

(Z)-5-Fluoro-2-Methyl-(4-Pyridazinylidene)-3-(N-2-Fluorobenzyl)-Indenylacetamide 5-Fluoro-2-methyl-3-(N-2-fluorobenzyl)-indenylacetamide from Example 15, part A is allowed to react with pryidazine-4-aldehyde according to the procedure of Example 1, Part G in order to obtain the title compound. Recrystallization gives the title compound ($R_1$=F, $R_2$=$CH_3$, $R_3$=H, $R_4$=H, $R_5$=H, $R_6$=H, $R_7$=F, n=1, m=1, Y=4-pyridazinyl).

EXAMPLE 23

(Z)-5-Fluoro-2-Methyl-(4-Pyridinylidene)-3-(N-(S-α-Hydroxymethyl)Benzyl)-Indenylacetamide (A) 5-Fluoro-2-methyl-3-(N-(S-α-hydroxylmethyl)benzyl)-indenylacetamide 5-Fluoro-2-methylindenyl-3-acetic acid (from Example 1D) (2.6 mmol) in DMA (2 ml) is allowed to react with n-(3-dimethylaminopropyl)-N'-ethylcarbodiimide hydrochloride (4 mmol) and S-2-amino-2-phenylethanol (3.5 mmol) at room temperature for two days. The reaction mixture is added dropwise to stirred ice water (50 ml). A white precipitate is filtered off, washed with water (5 ml), and dried in vacuo. Recrystallization from ethylacetate gives the desired compound.

(B) (Z)-5-fluoro-2-methyl-(4-pyridinylidene)-3-(N-(S-α-hydroxymethyl)benzyl)-indenylacetamide 5-Fluoro-2-methyl-3-(N-(S-α-hydroxylmethyl)benzyl)-indenylacetamide from part A is allowed to react with 4-pryidinecarboxaldehyde according to the procedure of Example 1, Part G in order to obtain the title compound. Recrystallization gives the title compound ($R_1$=F, $R_2$=$CH_3$, $R_3$=H, $R_4$=H, $R_5$=$CH_2OH$, $R_6$=H, $R_7$=H, n=1, m=1, Y=4-pyridinyl).

EXAMPLE 24

(Z)-5-Fluoro-2-Methyl-(3-Pyridinylidene)-3-(N-(S-α-Hydroxymethyl)Benzyl)-Indenylacetamide 5-Fluoro-2-methyl-3-(N-(S-α-hydroxylmethyl)benzyl)-indenylacetamide from Example 23 part A is allowed to react with 3-pryidinecarboxaldehyde according to the procedure of Example 1, Part G in order to obtain the title compound. Recrystallization gives the title compound ($R_1$=F, $R_2$=$CH_3$, $R_3$=H, $R_4$=H, $R_5$=$CH_2OH$, $R_6$=H, $R_7$=H, n=1, m=1, Y=3-pyridinyl).

EXAMPLE 25

(Z)-5-Fluoro-2-Methyl-(2-Pyridinylidene)-3-(N-(S-α-Hydroxymethyl)Benzyl)-Indenylacctamide 5-Fluoro-2-methyl-3-(N-(S-α-hydroxylmethyl)benzyl)-indenylacetamide from Example 23 part A is allowed to react with 2-pryidinecarboxaldehyde according to the procedure of Example 1, Part G in order to obtain the title compound. Recrystallization gives the title compound ($R_1$=F, $R_2$=$CH_3$, $R_3$=H, $R_4$=H, $R_5$=$CH_2OH$, $R_6$=H, $R_7$=H, n=1, m=1, Y=2-pyridinyl).

EXAMPLE 26

(Z)-5-Fluoro-2-Methyl-(4-Quinolinylidene)-3-(N-(S-α-Hydroxymethyl)Benzyl)-Indenylacetamide 5-Fluoro-2-methyl-3-(N-(S-α-hydroxylmethyl)benzyl)-indenylacetamide from Example 23 part A is allowed to react with 4-quinolinecarboxaldehyde according to the procedure of Example 1, Part G in order to obtain the title compound. Recrystallization gives the title compound ($R_1$=F, $R_2$=$CH_3$, $R_3$=H, $R_4$=H, $R_5$=$CH_2OH$, $R_6$=H, $R_7$=H, n=1, m=1, Y=4-quinolinyl).

EXAMPLE 27

(Z)-5-Fluoro-2-Methyl-(Pyrazidinylidene)-3-(N-(S-α-Hydroxymethyl)Benzyl)-Indenylacetamide 5-Fluoro-2-methyl-3-(N-(S-α-hydroxylmethyl)benzyl)-indenylacetamide from Example 23 part A is allowed to react with pryazidinecarboxaldehyde according to the procedure of Example 1, Part G in order to obtain the title compound. Recrystallization gives the title compound ($R_1$=F, $R_2$=$CH_3$, $R_3$=H, $R_4$=H, $R_5$=$CH_2OH$, $R_6$=H, $R_7$=H, n=1, m=1, Y=pyrazidinyl).

EXAMPLE 28

(Z)-5-Fluoro-2-Methyl -(3-Pyridazinylidene)-3-(N-(S-α-Hydroxymethyl)Benzyl)-Indenylacetamide 5-Fluoro-2-methyl-3-(N-(S-α-hydroxylmethyl)benzyl)-indenylacetamide from Example 23 part A is allowed to react with pryidazine-3-aldehyde according to the procedure of Example 1, Part G in order to obtain the title compound. Recrystallization gives the title compound ($R_1$=F, $R_2$=$CH_3$, $R_3$=H, $R_4$=H, $R_5$=$CH_2OH$, $R_6$=H, $R_7$=H, n=1, m=1, Y=3-pyridazinyl).

EXAMPLE 29

(Z)-5-Fluoro-2-Methyl-(4-Pyrimidinylidene)-3-(N-(S-α-Hydroxymethyl)Benzyl)-Indenylacetamide 5-Fluoro-2-methyl-3-(N-(S-α-hydroxylmethyl)benzyl)-indenylacetamide from Example 23 part A is allowed to react with pryimidine-4-aldehyde according to the procedure of Example 1, Part G in order to obtain the title compound. Recrystallization gives the title compound ($R_1$=F, $R_2$=$CH_3$, $R_3$=H, $R_4$=H, $R_5$=$CH_2OH$, $R_6$=H, $R_7$=H, n=1, m=1, Y=4-pyrimidinyl).

EXAMPLE 30

(Z)-5-Fluoro-2-Methyl -(4-Pyridazinylidene)-3-(N-(S-α-Hydroxymethyl)Benzyl)-Indenylacetamide 5-Fluoro-2-methyl-3-(N-(S-α-hydroxylmethyl)benzyl)-indenylacetamide from Example 23 part A is allowed to react with pryidazine-4-aldehyde according to the procedure of Example 1, Part G in order to obtain the title compound. Recrystallization gives the title compound ($R_1$=F, $R_2$=$CH_3$, $R_3$=H, $R_4$=H, $R_5$=$CH_2OH$, $R_6$=H, $R_7$=H, n=1, m=1, Y=4-pyridazinyl).

EXAMPLE 31 rac-(Z)-5-Fluoro-2-Methyl-(4-Pyridinylidene)-3-(N-Benzyl)Indenyl-α-Hydroxyacetamide (A) 5-fluoro-2-methyl-3-(N-benzyl-N-hydroxy)-indenylacetamide To a mixture of N-benzylhydroxylamine hydrochoride (12 mmol) and $Et_3N$ (22 mmol) in $CH_2Cl_2$ (100 ml) at 0° C.

is added a cold solution of 5-fluoro-2-methylindenyl-3-acetyl chloride (Example 1, Step E) (10 mmol) in CH$_2$Cl$_2$ (75 ml) over a period of 45–60 minutes. The mixture is warmed to room temperature and is stirred for 1 hour. The mixture is diluted with water (100 ml), and the organic layer is washed with HCl (2×25 ml) and brine (2×100 ml), dried (MgSO$_4$) and evaporated. The crude product is purified with flash chromatography to give the title compound.

(B) 5-Fluoro-2-methyl-3-(N-benzyl-N-mesyloxy)-indenylacetamide

To a solution of 5-fluoro-2-methyl-3-(N-benzyl-N-hydroxy)-indenylacetamide (5 mmol) in CH$_2$Cl$_2$ (25 ml) at 0° C. is added triethylamine (5 mmol). The mixture is stirred for 10 minutes, and methanesulfonyl chloride (5.5 mmol) is added dropwise. The solution is stirred at 0° C. for 2 hours, allowed to warm to room temperature, and stirred for another 2 hours. The organic layer is washed with water (2×20 ml), in HCl (15 ml), and brine (20 ml) and dried over MgSO$_4$. After rotary evaporation, the product is purified with flash chromatography to give the title compound.

(C) rac-5-Fluoro-2-methyl-3-(N-benzyl)-α-hydroxyindenylacetamide

To a solution of 5-fluoro-2-methyl-3-(N-benzyl-N-mesyloxy)-indenylacetamide (2 mmol) in CH$_3$CN/H$_2$O (12 ml. each) is added triethylamine (2.1 mmol) in CH$_3$CN (24 ml) over a period of 6 hours. The mixture is stirred overnight. The solvent is removed, and the residue diluted with ethyl acetate (60 ml), washed with water (4×20 ml), in HCl (15 ml), and brine (20 ml) and dried over MgSO$_4$. After rotary evaporation, the product is purified by recrystallization to give the title compound.

(D) rac-(Z)-5-Fluoro-2-methyl-(4-pyridinylidene)-3-(N-benzyl)-indenyl-α-hydroxyacetamide is obtained from rac-5-fluoro-2-methyl-3-(N-benzyl)-α-hydroxyindenylacetamide using the procedure of Example 1, Part G (R$_1$=F, R$_2$=CH$_3$, R$_3$=OH, R$_4$=H, R$_5$=H, R$_6$=H, R$_7$=H, n=1, m=1, Y=4-pyridinyl).

EXAMPLE 32

2-[(Z)-5-Fluoro-2-Methyl-(4-Pyridinylidene)-3-(N-Benzyl)-Indenyl]-Oxyacetamide

For Pfitzner-Moffatt oxidation, a solution of rac-(Z)-5-fluoro-2-methyl-(4-pyridinylidene)-3-(N-benzyl)-indenyl-α-hydroxyacetamide (1 mmol) in DMSO (5 ml) is treated with dicyclohexylcarbodiimide (3 mmol). The mixture is stirred overnight, and the solvent is evaporated. The crude product is purified by flash chromatography to give the title compound (R$_1$=F, R$_2$=CH$_3$, R$_3$ and R$_4$ together form C=O, R$_5$=H, R$_6$=H, R$_7$=H, n=1, m=1, and Y=4-pyridinyl).

EXAMPLE 33 rac-(Z)-5-Fluoro-2-Methyl-(4-Pyridinylidene)-3-(N-Benzyl)-Indenyl-α-(2-Propylamino)-Acetamide (A) 5-Fluoro-2-methyl-3-(N-2-propyl-N-hydroxy)-indenylacetamide is obtained from 5-fluoro-2-methylindenyl-3-acetyl chloride (Example 1, Step E) using the procedure of Example 31, Part A and replacing N-benzylhydroxylamine hydrochloride with N-2-propyl hydroxylamine hydrochloride.

(B) 5-Fluoro-2-methyl-3-(N-2-propyl-N-mesyloxy)-indenylacetamide is obtained according to the procedure of Example 31, Part B.

(C) rac-5-Fluoro-2-methyl-3-(N-benzyl)-α-(2-propylamino)-acetamide. To 5-fluoro-2-methyl-3-(N-2-propyl-N-mesyloxy)-indenylacetamide (2 mmol) in CH$_2$Cl$_2$ (25 ml) at 0° C. is added benzylamine (4.4 mmol) in CH$_2$Cl$_2$ (15 ml) over a period of 30 minutes. The resulting solution is stirred at 0° C. for 1 hour, and at room temperature overnight. The solvent is removed, and the residue is treated with 1 N NaOH, and is extracted with CH$_2$Cl$_2$ (100 ml). The extract is washed with water (2×10 ml), and is dried over MgSO$_4$. After rotary evaporation, the product is purified by flash chromatography.

(D) rac-(Z)-5-Fluoro-2-methyl-(4-pyridinylidene)-3-(N-benzyl)-indenyl-α-(2-propylamino)-acetamide is obtained from rac-5-fluoro-2-methyl-3-(N-benzyl)-α-(2-propylamino)-acetamide using the procedure of Example 1, Part G (R$_1$=F, R$_2$=CH$_3$, R$_3$=isopropylamino, R$_4$=H, R$_5$=H, R$_6$=H, R$_7$=H, n=1, m=1, Y=4-pyridinyl).

EXAMPLE 34

(Z)-6-Methoxy-2-Methyl-(4-Pyridinylidene)-3-(N-Benzyl)-Indenylacetamide (A) Ethyl-2-Hydroxy-2-(p-Methoxyphenyl)-1-Methylpropionate In a 500 ml. 3-necked flask is placed 36.2 g. (0.55 mole) of zinc dust, a 250 ml. addition funnel is charged with a solution of 80 ml. anhydrous benzene, 20 ml. of anhydrous ether, 80 g. (0.58 mole) of p-anisaldehyde and 98 g. (0.55 mole) of ethyl-2-bromoprolonate. About 10 ml. of the solution is added to the zinc dust with vigorous stirring, and the mixture is warmed gently until an exothermic reaction commences. The remainder is added dropwise at such a rate that the reaction mixture continues to reflux smoothly (ca. 30–35 min.). After addition is completed the mixture is placed in a water bath and refluxed for 30 minutes. After cooling to 0°, 250 ml. of 10% sulfuric acid is added with vigorous stirring. The benzene layer is extracted twice with 50 ml. portions of 5% sulfuric acid and washed twice with 50 ml. portions of water. The combined aqueous acidic layers are extracted with 2×50 ml. ether. The combined etheral and benzene extracts are dried over sodium sulfate. Evaporation of solvent and fractionation of the residue through a 6" Vigreux column affords 89 g. (60%) of the product, ethyl-2-hydroxy-2-(p-methoxyphenyl)-1-methylpropionate, B.P. 165–160° (1.5 mm.).

(B) 6-Methoxy-2-methylindanone

By the method described in Vander Zanden, Rec. Trav. Chim., 68, 413 (1949), the compound from part A is converted to 6-methoxy-2-methylindanone.

Alternatively, the same compound can be obtained by adding α-methyl-β-(p-methoxylphenyl)propionic acid (15 g.) to 170 g. of polyphosphoric acid at 50° and heating the mixture at 83–90° for two hours. The syrup is poured into iced water. The mixture is stirred for one-half hour, and is extracted with ether (3×). The etheral solution is washed with water (2×) and 5% NaHCO$_3$ (5×) until all acidic material has been removed, and is dried over sodium sulfate. Evaporation of the solution gives 9.1 g. of the indanone as a pale yellow oil.

(C) (Z)-6-Methoxy-2-methyl-(4-pyridinylidene)-3-(N-benzyl)-indenylacetamide

In accordance with the procedures described in Example 1, parts D–G, this compound is obtained substituting 6-methoxy-2-methylindanone for 6-fluoro-2-methylindanone in part D of Example 1.

EXAMPLE 35

(Z)-5-Methoxy-2-Methyl-(4-Pyridinylidene)-3-(N-Benzyl)-Indenylacetamide (A) Ethyl 5-Methoxy-2-Methyl-3-Indenyl Acetate A solution of 13.4 g of 6-methoxy-2-methylindanone and 21 g. of ethyl bromoacetate in 45 ml. benzene is added over a period of five minutes to 21 g. of zinc amalgam (prepared according to Org. Syn. Coll. Vol. 3) in 110 ml. benzene and 40 ml. dry ether. A few cyrstals of iodine are added to start the reaction, and the reaction mixture is maintained at reflux temperature (ca. 65°) with external heating. At three-hour intervals, two batches of 10 g. zinc amalgam and 10 g. bromoester are added and the mixture is then refluxed for 8 hours. After addition of 30 ml. of ethanol and 150 ml. of acetic acid, the mixture is poured into 700 ml. of 50% aqueous acetic acid. The organic layer is separated, and the aqueous layer is extracted twice with ether. The combined organic layers are washed thoroughly with water, ammonium hydroxide and water. Drying over sodium sulfate, evaporation of solvent in vacuo followed by pumping at 80° (bath temperature)(1–2 mm.) gives crude ethyl-(1-hydroxy-2-methyl-6-methoxy-indenyl) acetate (ca. 18 g.).

A mixture of the above crude hydroxyester, 20 g. of p-toluenesulfonic acid monohydrate and 20 g. of anhydrous calcium chloride in 250 ml. toluene is refluxed overnight. The solution is filtered, and the solid residue is washed with toluene. The combined toluene solution is washed with water, sodium bicarbonate, water and then dried over sodium sulfate. After evaporation, the crude ethyl 5-methoxy-2-methyl-3-indenyl acetate is chromatographed on acid-washed alumina, and the product is eluted with petroleum ether-ether (v./v. 50–100%) as a yellow oil (11.8 g., 70%).

(B) (Z)-5-Methoxy-2-methyl-(4-pyridinylidene)-3-(N-benzyl)-indenylacetamide

In accordance with the procedures described in Example 1, parts E–G, this compound is obtained substituting ethyl-5-methoxy-2-methyl-3-indenyl acetate for 5-fluoro-2-methindenyl-3-acetic acid in Example 1, part E.

EXAMPLE 36

(Z)-α-5-Methoxy-2-Methyl-(4-Pyidinylidene)-3-(N-Benzyl)-Indenylpropionamide (A) α-(5-Methoxy-2-methyl-3-indenyl)propionic acid The procedure of Example 35, part (A) is followed using ethyl α-bromopropionate in equivalent quantities in place of ethyl bromoacetate used therein. There is obtained ethyl α-(1-hydroxy-6-methoxy-2-methyl-1-indanyl)propionate, which is dehydrated to ethyl α-(5-methoxy-2-methyl-3-indenyl)propionate in the same manner.

The above ester is saponified to give α-(5-methoxy-2-methyl-3-indenyl)propionic acid.

(B) (Z)-α-5-Methoxy-2-methyl-(4-pyridinyl)-3-(N-benzyl)-α-methyl indenylpropionamide In accordance with the procedures described in Example 1, parts E–G, this compound is obtained substituting α-5-methoxy-2-methyl-3-indenyl)propionic acid for 5-fluoro-2-methylindenyl-3-acetic acid in Example 1, part E.

EXAMPLE 37

(Z) α-Fluoro-5-Methoxy-2-Methyl-(4-Pyridinylidene)-3-(N-Benzyl)Indenylacetamide (A) Methyl-5-Methoxy-2-Methyl-3-Indenyl-α-Fluoro Acetate A mixture of potassium fluoride (0.1 mole) and methyl-5-methoxy-2-methyl-3-indenyl-α-tosyloxy acetate (0.05 mole) in 200 ml. dimethylformamide is heated under nitrogen at the reflux temperature for 2–4 hours. The reaction mixture is cooled, poured into iced water and then extracted with ether. The ethereal solution is washed with water, sodium bicarbonate and dried over sodium sulfate. Evaporation of the solvent and chromatography of the residue on an acid-washed alumina column (300 g.) using ether-petroleum ether (v./v. 20–50%) as eluent give the product, methyl-5-methoxy-2-methyl-3-indenyl-α-fluoroacetate.

(B) (Z) α-Fluoro-5-methoxy-2-methyl-(4-pyridinylidene)-3-(N-benzyl)indenylacetamide In accordance with the procedures described in Example 1, parts E–G, this compound is obtained substituting methyl-5-methoxy-2-methyl-3-indenyl-α-fluoroacetate for 5-fluoro-2-methylindenyl-3-acetic acid in Example 1, part E.

For the introduction of the =CH—Y part in Scheme III, any of the appropriate heterocyclic aldehydes may be used either directly in the base-catalyzed condensation or in a Wittig reaction in an alternative route. The aldehydes that may be used are listed in Table 1 below:

TABLE 1 pyrrol-2-aldehyde*
pyrimidine-2-aldehyde
6-methylpyridine-2-aldehyde*
1-methylbenzimidazole-2-aldehyde
isoquinoline-4-aldehyde
4-pyridinecarboxaldehyde*
3-pyridinecarboxaldehyde*
2-pyridinecarboxaldehyde*
4,6-dimethyl-2-pyridinecarboxaldehyde*
4-methyl-pyridinecarboxaldehyde*
4-quinolinecarboxaldehyde*
3-quinolinecarboxaldehyde*
2-quinolinecarboxaldehyde*
2-chloro-3-quinolinecarboxaldehyde*
pyrazinealdehyde
(Prepared as described by Rutner et al., JOC 1963, 28, 1898–99)
pyridazine-3-aldehyde
(Prepared as described by Heinisch et al., Monatshefte Fuer Chemie 108, 213–224,1977)
pyrimidine-4-aldehyde
(Prepared as described by Bredereck et al., Chem. Ber. 1964, 97, 3407–17)
2-methyl-pyrimidine-4-aldehyde
(Prepared as described by Bredereck et al., Chem. Ber. 1964, 97, 3407–17)
pyridazine-4-aldehyde
(Prepared as described by Heinisch et al., Monatshefte Fuer Chemie 104, 1372–1382 (1973))
1-methylindole-3-carboxaldehyde*
1-acetyl-3-indolecarboxaldehyde*

*Available from Aldrich

The aldehydes above can be used in the reaction schemes above in combination with various appropriate amines to produce compounds with the scope of this invention. Examples of appropriate amines are those listed in Table 2 below:

TABLE 2 benzylamine
2,4-dimethoxybenzylamine
2-methoxybenzylamine
2-fluorobenzylamine
4-dimethylaminobenzylamine
4-sulfonaminobenzylamine
1-phenylethyamine (R-enantiomer)
2-amino-2-phenylethanol (S-enantiomer)
2-phenylglycinonitrile (S-enantiomer)

EXAMPLE 38

(Z)-5-Fluoro-2-Methyl-(4-Pyridylidene)-3-(N-Benzyl)Indenylacetamide Hydrochloride (Z)-5-Fluoro-2-methyl-(4-pyridylidene)-3-(N-benzyl) indenylacetamide (1396 g; MW 384.45; 3.63 mol) from Example 1 is dissolved at 45° C. in ethanol (28 L). Aqueous HCl (12 M; 363 mL) is added stepwise. The reaction mixture is heated under reflux for 1 hour, is allowed to cool to room temperature, then stored at −10° C. for 3 hours. The resulting solid is filtered off, is washed with ether (2×1.5 L) and is air-dried overnight. Drying under vacuum at 70° C. for 3 days gives (Z)-5-fluoro-2-methyl-(4-pyridylidene)-3-(N-benzyl)indenylacetamide hydrochloride with a melting point of 207–209° C. ($R_1$=F, $R_2$=$CH_3$, $R_3$=H, $R_4$=H, $R_5$=H, $R_6$=H, $R_7$=H, n=1, m=1, Y=4-pyridinyl.hydrochloride). Yield: 1481 g (97%; 3.51 mol); MW: 420.91 g/mol.

$^1$H-NMR (DMSO-$d_6$): 2.18 (s,3,=C—$CH_3$); 3.54 (s,2, =$CH_2$CO); 4.28 (d,2,$NCH_2$); 6.71 (m,1,ar.); 7.17 (m,8,ar.); 8.11 (d,2,ar., AB system); 8.85 (m,1,NH); 8.95 (d,2,ar.,AB system); IR (KBr): 3432 NH; 1635 C=O; 1598 C=C.

EXAMPLE 39

(Z)-5-fluoro-2-methyl-(4-pyridylidene)-3-(N-benzyl)-indenylacetamide p-methylbenzenesulfonate (Z)-5-fluoro-2-methyl-(4-pyridylene)-3-(N-benzyl) indenylacetamide (MW=384.46 g/mol; 5.21 mmol; 2 g) from Example 1 is dissolved in ethanol (50 ml). Solid p-toluenesulfonic acid monohydrate (MW=190.22 g/mol; 5.21 mmol; 991 mg) is added to the stirred solution. The reaction mixture is stirred for 12 hours at room temperature. The ethanol is evaporated in aspirator vacuum. The residue is dried in high vacuum to yield (Z)-5-fluoro-2-methyl-(4-pyridylidene)-3-(N-benzyl)-indenylacetamide p-methylbenzenesulfonate as an orange-red powder.

As to identifying structurally additional PDE2 and PDE5 inhibiting compounds besides those of Formula I that can be effective therapeutically for IBD, one skilled in the art has a number of useful model compounds disclosed herein (as well as their analogs) that can be used as the bases for computer modeling of additional compounds having the same conformations but different chemically. For example, software such as that sold by Molecular Simulations Inc. release of WebLab® ViewerPro™ includes molecular visualization and chemical communication capabilities. Such software includes functionality, including 3D visualization of known active compounds to validate sketched or imported chemical structures for accuracy. In addition, the software allows structures to be superimposed based on user-defined features, and the user can measure distances, angles, or dihedrals.

In this situation, since the structures of active compounds are disclosed above, one can apply cluster analysis and 2D and 3D similarity search techniques with such software to identify potential new additional compounds that can then be screened and selected according to the selection criteria of this invention. These software methods rely upon the principle that compounds, which look alike or have similar properties, are more likely to have similar activity, which can be confirmed using the PDE selection criterion of this invention.

Likewise, when such additional compounds are computer-modeled, many such compounds and variants thereof can be synthesized using known combinatorial chemistry techniques that are commonly used by those of ordinary skill in the pharmaceutical industry. Examples of a few for-hire combinatorial chemistry services include those offered by New Chemical Entities, Inc. of Bothell Wash., Protogene Laboratories, inc., of Palo Alto, Calif., Axys, Inc. of South San Francisco, Calif., Nanosyn, Inc. of Tucson, Ariz., Trega, Inc. of San Diego, Calif., and RBI, Inc. of Natick, Mass. There are a number of other for-hire companies. A number of large pharmaceutical companies have similar, if not superior, in-house capabilities. In short, one skilled in the art can readily produce many compounds for screening from which to select promising compounds for treatment of neoplasia having the attributes of compounds disclosed herein.

To further assist in identifying compounds that can be screened and then selected using the criterion of this invention, knowing the binding of selected compounds to PDE5 and PDE2 protein is of interest. By the procedures discussed below, it is believed that that preferable, desirable compounds meeting the selection criteria of this invention bind to the cGMP catalytic regions of PDE2 and PDE5.

To establish this, a PDE5 sequence that does not include the catalytic domain can be used. One way to produce such a sequence is to express that sequence as a fusion protein, preferably with glutiathione S-transferase ("GST"), for reasons that will become apparent.

RT-PCR method is used to obtain the cGB domain of PDE5 with forward and reverse primers designed from bovine PDE5A cDNA sequence (McAllister-Lucas L. M. et al, J. Biol. Chem. 268, 22863–22873, 1993) and the selection among PDE 1–10 families. 5'-3', Inc. kits for total RNA followed by oligo (dT) column purification of mRNA are used with HT-29 cells. Forward primer (GAA-TTC-TGT-TAG-AAA-AGC-CAC-CAG-AGA-AAT-G, 203–227) and reverse primer (CTC-GAG-CTC-TCT-TGT-TTC-TTC-CTC-TGC-TG, 1664–1686) are used to synthesize the 1484 bp fragment coding for the phosphorylation site and both low and high affinity cGMP binding sites of human PDE5A (203–1686 bp, cGB-PDE5). The synthesized cGB-PDE5 nucleotide fragment codes for 494 amino acids with 97% similarity to bovine PDE5A. It is then cloned into pGEX-5X-3 glutathione-S-transferase (GST) fusion vector (Pharmacia Biotech) with tac promoter, and EcoRI and XhoI cut sites. The fusion vector is then transfected into E. Coli BL21 (DE3) bacteria (Invitrogen). The transfected BL21 bacteria is grown to log phase, and then IPTG is added as an inducer. The induction is carried at 20° C. for 24 hrs. The bacteria are harvested and lysed. The soluble cell lysate is incubated with GSH conjugated Sepharose 4B (GSH-Sepharose 4B). The GST-cGB-PDE5 fusion protein can bind to the GSH-Sepharose beads, and the other proteins are washed off from beads with excessive cold PBS.

The expressed GST-cGB-PDE5 fusion protein is displayed on 7.5% SDS-PAGE gel as an 85 Kd protein. It is characterized by its cGMP binding and phosphorylation by protein kinases G and A. It displays two cGMP binding sites, and the $K_d$ is 1.6±0.2 $\mu$M, which is close to $K_d$=1.3 $\mu$M of the native bovine PDE5. The GST-cGB-PDE5 on GSH-conjugated sepharose beads can be phosphorylated in vitro by cGMP-dependent protein kinase and cAMP-dependent protein kinase A. The $K_m$ of GST-cGB-PDE5 phosphorylation by PKG is 2.7$\mu$M and Vmax is 2.8 $\mu$M, while the $K_m$ of BPDEtide phosphorylation is 68 $\mu$M. The phosphorylation by PKG shows molecular phosphate incorporated into GST-cGB-PDE5 protein on a one-to-one ratio.

A cGMP binding assay for compounds of interest (Francis S. H. et al, J. Biol. Chem. 255, 620–626, 1980) is done in a total volume of 100 $\mu$L containing 5 mM sodium phosphate buffer (pH=6.8), 1 mM EDTA, 0.25 mg/mL BSA, $H^3$-cGMP (2 $\mu$M, NEN) and the GST-cGB-PDE5 fusion protein (30 $\mu$g/assay). Each compound to be tested is added at the same time as $^3$H-cGMP substrate, and the mixture is incubated at 22° C. for 1 hour. Then, the mixture is transferred to Brandel MB-24 cell harvester with GF/B as the filter membrane followed by 2 washes with 10 mL of cold 5 mM potassium buffer(pH 6.8). The membranes are then cut out and transferred to scintillation vials followed by the addition of 1 mL of $H_2O$ and 6 mL of Ready Safe™ liquid scintillation cocktail to each vial. The vials are counted on a Beckman LS 6500 scintillation counter.

For calculation, blank samples are prepared by boiling the binding protein for 5 minutes, and the binding counts are <1% when compare to unboiled protein. The quenching by filter membrane or other debris are also calibrated.

PDE5 inhibitors, sulindac sulfide, exisulind, E4021 and zaprinast, and cyclic nucleotide analogs, cAMP, cyclic IMP, 8-bromo-cGMP, cyclic UMP, cyclic CMP, 8-bromo-cAMP, 2'-O-butyl-cGMP and 2'-O-butyl-cAMP were selected to test whether they could competitively bind to the cGMP binding sites of the GST-cGB-PDE5 protein. cGMP specifically bound to GST-cGB-PDE5 protein. Cyclic AMP, cUMP, cCMP, 8-bromo-cAMP, 2'-O-butyl-cAMP and 2'-O-butyl-cGMP did not compete with cGMP in binding. Cyclic IMP and 8-bromo-cGMP at high concentration (100 $\mu$M) can partially compete with cGMP (2 $\mu$M) binding. None of the PDE5 inhibitors showed any competition with cGMP in binding of GST-cGB-PDE5. Therefore, they do not bind to the cGMP binding sites of PDE5.

However, Compound 38 does competitively (with cGMP) bind to PDE 5. Given that Compound 38 does not bind to the cGMP-binding site of PDE5, the fact that there is competitive binding between Compound 38 and cGMP at all means that desirable compounds such as Compound 38 bind to the cGMP catalyic site on PDE5, information that is readily obtainable by one skilled in the art (with conventional competitive binding experiments) but which can assist one skilled in the art more readily to model other compounds. Thus, with the chemical structures of desirable compounds presented herein and the cGMP binding site information, one skilled in the art can model, identify and select (using the selection criteria of this invention) other chemical compounds for use as therapeutics.

Biological Effects (A) Cyclooxygenase (COX) Inhibition

COX catalyzes the formation of prostaglandins and thromboxane by the oxidative metabolism of arachidonic acid. The compound of Example 1 of this invention, as well as a positive control, (sulindac sulfide) were evaluated to determine whether they inhibited purified cyclooxygenase Type I (see Table 1 below).

The compounds of this invention were evaluated for inhibitory effects on purified COX. The COX was purified from ram seminal vesicles, as described by Boopathy, R. and Balasubramanian, J., 239:371–377, 1988. COX activity was assayed as described by Evans, A. T., et al., "Actions of Cannabis Constituents on Enzymes Of Arachidonate Metabolism Anti-Inflammatory Potential," Biochem. Pharmacol., 36:2035–2037, 1987. Briefly, purified COX was incubated with arachidonic acid (100 $\mu$M) for 2.0 min at 37° C. in the presence or absence of test compounds. The assay was terminated by the addition of TCA, and COX activity was determined by absorbance at 530 nm.

TABLE 1

| EXAMPLE | COX I<br>% Inhibition (100 $\mu$M) |
|---|---|
| Sulindac sulfide | 86 |
| 1 | <25 |

The advantage of very low COX inhibition is that compounds of this invention can be administered to patients without the side effects normally associated with COX inhibition.

(B) cGMP PDE Inhibition

Compounds of this invention are also PDE2 and PDE5 inhibitors as taught in part U.S. patent application Ser. No. 09/046,739 filed Mar. 24, 1998. Compounds can be tested for inhibitory effect on phosphodiesterase activity using either the enzyme isolated from any tumor cell line such as HT-29 or SW-480. Phosphodiesterase activity can be determined using methods known in the art, such as a method using radioactive $^3$H cyclic GMP (cGMP)(cyclic 3',5'-guanosine monophosphate) as the substrate for PDE5 enzyme. (Thompson, W. J., Teraski, W. L., Epstein, P. M., Strada, S. J., Advances in Cyclic Nucleotide Research, 10:69–92, 1979, which is incorporated herein by reference). In brief, a solution of defined substrate $^3$H-cGMP specific activity (0.2 $\mu$M; 100,000 cpm; containing 40 mM Tris-HCl (pH 8.0), 5 mM $MgCl_2$ and 1 mg/ml BSA) is mixed with the drug to be tested in a total volume of 400 $\mu$l. The mixture is incubated at 30° C. for 10 minutes with partially purified cGMP-specific PDE isolated from HT-29 cells. Reactions are terminated, for example, by boiling the reaction mixture for 75 seconds. After cooling on ice, 100 $\mu$l of 0.5 mg/ml snake venom (O. Hannah venom available from Sigma) is added and incubated for 10 min at 30° C. This reaction is then terminated by the addition of an alcohol, e.g. 1 ml of 100% methanol. Assay samples are applied to a anion chromatography column (1 ml Dowex, from Aldrich) and washed with 1 ml of 100% methanol. The amount of radioactivity in the breakthrough and the wash from the columns in then measured with a scintillation counter. The degree of PDE5 inhibition is determined by calculating the amount of radioactivity in drug-treated reactions and comparing against a control sample (a reaction mixture lacking the tested compound).

Using such protocols, the compound of Example 1 had an $IC_{50}$ value for PDE5 inhibition of 0.68 $\mu$M. Using similar protocols, the compound of Example 38 ("Compound 38") had an $IC_{50}$ value for PDE2 of 14 $\mu$M, an $IC_{50}$ value for PDE5 of 4 $\mu$M, an $IC_{50}$ value for PDE1 of 3 $\mu$M, and an $IC_{50}$ value for PDE4 of 6 $\mu$M.

(C) Safety Assessment in Mammals

As one skilled in the art will recognize from the data presented below, Compound 38 can safely be given to animals at doses far beyond the tolerable (and in many cases toxic) doses of conventional IBD therapies. For example, in an acute toxicity study in rats, single oral doses of Compound 38 administered (in a 0.5% carboxy-methylcellulose vehicle) at doses up to and including 2000 mg/kg resulted in no observable signs of toxicity. At 2000 mg/kg, body weight gains were slightly reduced. A single dose of 1000 mg/kg administered intraperitoneally resulted in reduced body weight gain, with mesenteric adhesions seen in some animals from this group at necropsy.

In dogs, the administration of Compound 38 in capsules at 1000 mg/kg resulted in no signs of toxicity to the single group of two male and two female dogs. Due to the nature of Compound 38 capsules, this dose necessitated the use of at least 13 capsules to each animal, which was judged to be the maximum number without subjecting the animals to stress. Therefore, these dogs were subsequently administered seven consecutive doses of 1000 mg/kg/day. At no time in either dosing phase were any obvious signs of drug-related effects observed.

Thus, on a single-dose basis, Compound 38 is not acutely toxic. Based on the findings of these studies, the oral $LD_{50}$ of Compound 38 was considered to be greater than 1000 mg/kg in dogs and 2000 mg/kg in rats, and the intraperitoneal $LD_{50}$ was considered to be greater than 1000 mg/kg in rats.

A seven-day dose-range finding study in rats, where Compound 38 was evaluated by administering it at doses of 0, 50, 500 or 2000 mg/kg/day resulting in no observable signs of toxicity at 50 mg/kg/day. At 500 mg/kg/day, treatment-related effects were limited to an increase in absolute and relative liver weights in female rats. At 2000 mg/kg/day, effects included labored breathing and/or abnormal respiratory sounds, decreased weights gains and food consumption in male rats, and increased liver weights in female rats. No hematological or blood chemistry changes nor any microscopic pathology changes, were seen at any dose level.

A 28-day study in rats was also carried out at 0, 50, 500 and 2000 mg/kg/day. There were no abnormal clinical observations attributed to Compound 38, and body weight changes, ophthalmoscopic examinations, hematological and blood chemistry values and urinalysis examinations were unremarkable. No macroscopic tissue changes were seen at necropsy. Organ weight data revealed statistically significant increase in liver weights at 2000 mg/kg/day, and statistically significant increases in thyroid weights for the 2000 mg/kg/day group. The slight liver and thyroid increases at the lower doses were not statistically significant. Histopathological evaluation of tissues indicated the presence of traces of follicular cell hypertrophy, increased numbers of mitotic figures (suggestive of possible cell proliferation) in the thyroid gland and mild centrilobular hypertrophy in the liver. These changes were generally limited to a small number of animals at the 2000 mg/kg/day dose, although one female at 500 mg/kg/day had increased mitotic figures in the thyroid gland. The findings in the liver may be indicative of a very mild stimulation of liver microsomal enzymes, resulting in increased metabolism of thyroid hormones, which in turn resulted in thyroid stimulation.

A long-term safety assessment study was conducted in rats to investigate Compound 38 at 50, 200 and 500 mg/kg/day following repeated oral dosing for 91 consecutive days. Orally administered Compound 38 did not produce any major toxicological effects in rats. The only finding was a dose-related trend to increased liver and thyroid/parathyroid weights noted in males and females at 200 and 500 mg/kg/day. Microscopically, slight hepatocellular hypertrophy at 200 and 500 mg/kg/day groups, follicular cell hypertrophy at 500 mg/kg/day and increase in accumulation of hyalin droplets in the kidneys at 200 and 500 mg/kg/day group. However, no changes in clinical biochemistry and hematology were evident. These changes were not associated with any gross clinical abnormality.

Dogs were also dosed orally with Compound 38 at 50, 150 and 300 mg/kg/day for 91 consecutive days. There were no toxicological effects in the dog following 91 days of dosing. Orange discoloration of the feces (same color as Compound 38) was seen in the 150 and 300 mg/kg/day groups. This finding suggested that most of Compound 38 was being eliminated via the feces. Slightly lowered body weights were noted in the highest dose group. This dose was also associated with increased liver weights. However, there were no microscopic alterations to support the increase in liver weight. Therefore, we concluded that Compound 38 is well tolerated in the dog.

Finally as to safety, in a single, escalating dose human clinical trial, patients, human safety study in which the drug was taken orally, Compound 38 produced no significant side effects at any dose (i.e., 50 mg BID, 100 mg BID, 200 mg BID and 400 mg BID).—doses above the level believed to be therapeutic for human IBD patients.

One skilled in the art should recognize that any of the side effects observed in these safety studies occurred at very high doses, in excess of recommended human doses and are extremely minimal compared to what one would expect at similar doses of conventional IBD therapies.

(D) Efficacy for IBD

IBD in humans is quite similar to IBD in dogs. See, Van Kruiningen, J. H., "Canine Colitis Comparable to Regional Enteritis and Colitis of Man," *Gastroenterology* 42(6): 1128–1142 (1972). In fact, the IBD treatments used in dogs are very similar to those used in humans, and the success rates are similarly disappointing. The number of dogs with IBD is estimated to be in the millions in the U.S. Feline IBD is also quite common.

Hence, for proof of principle for both humans and companion animals, we commenced a trial involving Compound 38 in seven dogs. The pre-drug history and results achieved with the drug in each dog are as follows:

History and Treatment of Dog #1

Summary:

Female, spayed 10½ year-old Old English Sheepdog. Dog #1 was near death after a 4-month history of severe IBD (in the form of severe lymphoplasmacytic enteritis) unresponsive to conventional therapy prior to receiving a drug of this invention. During 6 weeks of combined conventional therapy and Compound 38 (800 mg, BID) followed by 6 weeks of Compound 38 (800 mg, BID) alone, dog #1 steadily improved, regained at least 13 lbs. and became clinically normal. There was also significant histopathological improvement as discussed below and demonstrated in FIGS. 1–4. The four-month history (and the follow-on therapy on Compound 38) involved the following:

Month 1 (start): Weight 66 lbs. Dog #1 had a prior two-week history of inappetance, weight loss and pudding-like stools that would respond temporarily to symptomatic treatment with Pepto-Bismol and bland diet, then the same symptoms would recur. The dog had flatulence and increased lung sounds. Vomiting was observed once during the 2 week period. Initial blood test results CP/CBC/T4e {Chemistry Profile/Complete Blood Count/Thyroid hormone test} (abnormals only): ALT=406, alk Phos=80. Dog was on monthly milbemycin oxime for heartworm prevention/parasiticide. Thoracic radadiographs & ECG were unremarkable, with no cardiac abnormalities. Elevated liver enzymes were found, but were due to unknown factor (s).

Month 1 (middle): Weight 65 lbs. After treatment with prescription diet once a day, amoxicillin, and milk thistle, dog #1 was still inappetant. Repeated CP/CBC~all were within normal limits. Treating veterinarian recommended 200 mg cimetidine (Tagamet) BID, continued prescription diet and milk thistle.

Month 2: Dog #1 had intermittent anorexia, foul gas, and fluid diarrhea. Fecal flotation was negative but increased bacteria on slide/cytology was found. The treating veterinarian suspected some small intestinal bacterial overgrowth. 500 mg metronidazole BID and tylosin powder BID were prescribed. Nine days later, the owner reported that the dog was "a little better, eating more."

Month 3 (start): Dog was cachectic and weighed 56 lbs. Owner reported that the dog was inappetant (only eating small amount when hand fed) but otherwise not acting at all sick and not seeing diarrhea at that time. Repeated CP/CBC: ALT=86, alkPhos=90, chol=138 (L), WBC=9600 w/89% neuts, 5%LC (absolute count=480 lymphopenia). Owner believed that the dog may have lost as much as 20 pounds since about three months previously. Stool was normal.

Month 3 (middle): Weight 46 lbs. Double cavity ultrasound exam by board certified radiologist revealed thorax: normal, abdomen: echotexture, and size of liver: normal, spleen: normal but slightly increased in size, probable enlarged abdominal lymph nodes, mild to moderate distension of bowel. The treating veterinarian had concerns about inflammation and neoplasia. The primary diagnosis was lymphosarcoma. The radiologist recommended additional diagnostics and exploratory laparotomy was scheduled.

Month 3 (end): Weight 47.7 lbs. Exploratory surgery was performed: Abdominal lymph node appeared normal in size, liver slightly orange in appearance, samples were taken of liver, stomach and small intestine and samples divided and sent for histopathology. The histopathological diagnosis was severe lymphoplasmacytic and histiocytic enteritis (complete villous atrophy and severe diffuse loss of crypts). Special stains to identify any underlying etiologic agent were unrewarding.

Month 4 (start): Dog #1 was started on 250 mg sulfasalazine TID and 500 mg metronidazole BID because of severe foul fluid diarrhea.

Month 4 (middle) No significant improvement had been noted. 800 mg Compound 38 BID was begun. Conventional treatment was continued.

Month 5 (start): Owner reported that dog was much better, more energetic, eating normal food and stool was soft and semi-formed.

Month 5 (middle): Weight 53 lbs. Dog was clinically normal and gaining weight steadily. Flatulence continued to be a problem and amoxicillin and prozyme were dispensed for one week. The treating veterinarian discontinued metronidazole therapy and began weaning the dog off sulfasalazine.

Month 6 (start): The dog had its last dose sulafasalazine. Dog continued on Compound 38 alone for the next 6 weeks.

Month 7 (middle): Weight 57.3 lbs. Owner consented to follow-up laparotomy and biopsies were obtained from liver, 3 sites in jejunum near previous sample sites, duodenum, and ileum. Histopathologic diagnosis: subacute moderate mucosal enteritis, villi appeared shortened. (ALT=113, alkPhos=115 pre-surgery.)

Month 8 (start): Weight 60 lbs. Suture removal. Dog was healthy, and clinically normal after six weeks of combined conventional treatment plus Compound 38 followed by six weeks of Compound 38 alone. Dog was no longer on a prescription diet.

History and Treatment of Dog #2

Summary:

Male, neutered, 5 year-old Yorkshire Terrier with moderate IBD (in the form of plasmacytic enteritis) with mild lymphangiectasia causing double cavity effusions secondary to hypoproteinemia. Clinically normal after a two-week course of conventional therapy with antibiotics and prednisone followed by 7 weeks of Compound 38 (400 mg, BID) alone.

Dog #2 presented to referring veterinarian for chronic diarrhea unresponsive to metronidazole and symptomatic therapy that had progressed, causing hypoproteinemia, secondary cough and ascites. Surgical biopsies were obtained after 8 days of prednisone and antibiotic therapy. Prednisone and conventional therapy stopped after about two weeks and 400 mg Compound 38 BID alone started about a week later. After 7 weeks on Compound 38, dog #2 was clinically normal (including cessation of diarrhea) and blood protein levels returned to normal.

History and Treatment of Dog #3

Summary: Female spayed, 11¾ year-old Yorkshire Terrier with protein-losing enteropathy associated with IBD and double cavity effusions secondary to hypoproteinemia. The dog becameclinically normal after 7 weeks of Compound 38 (400mg. BID) with intermittent symptomatic therapy of metronidazole, but no conventional prednisone therapy.

Dog #3 presented with chief complaint of coughing, vomiting, diarrhea and hypoproteinemia. Fluid diarrhea and cough continued, full blood chemistry revealed continued hypoproteinemia. Radiographs revealed double cavity effusions, peritoneal and pleural fluid were present. Tentative diagnosis of protein-losing enteropathy with possible lymphangiectasia (due to breed predisposition) was made. Owner declined biopsies. Dog was treated with conventional treatment for 5–7 days (metronidazole and tylosin). About two and one-half weeks after first presenting, dog #3 was started on 400 mg Compound 38 BID alone.

During the subsequent two months, dog #3 required two 5–7 day courses of metronidazole and Pepto-Bismol because of diarrhea, including one bout that followed the owner feeding the dog barbecued steak. Dog ate home cooked meals and refused dog food (which is normal for this breed) and hence was not on a well-controlled diet. Clinically, dog was doing well. There was no further coughing and no evident ascites. Blood protein levels have gradually returned to within normal limits. The treating veterinarian commented after the dog's treatment with Compound 38: "This syndrome is difficult to manage conventionally with prednisone. [Dog #3] is now clinically normal [no diarrhea] despite no treatment with corticosteroids."

History and Treatment of Dog #4

Summary:

Female spayed, 6 year-old Chinese Shar-Pei with a 3½-year history of chronic IBD that could not be controlled with tylosin and diet. After withdrawal of conventional therapy and 7 weeks of Compound 38 (800 mg. BID), dog #4 was completely clinically normal with no signs of IBD.

Dog #4 had been receiving tylosin, metronidazole and prescription low residue diet high in fructooligosaccharides for about three years for tentative diagnosis of chronic IBD (no biopsies—Shar-Pei have recognized predilection for lymphocytic plasmacytic ententis). The dog's symptoms included tenesmus and mucoid-coated, unusually small but formed stools. Tylosin was stopped, and, prior to therapy with Compound 38, the owner noted return to consistently abnormal, mucoid-covered, small stools with some straining on defecation. 800 mg Compound 38 BID was started. After 7 weeks on the new therapy, the owner reported dog was clinically normal with normal size stool with no mucus. Owner also reported that "these are first perfectly normal stools dog has had in years and there has been no straining."

History and Treatment of Dog #5

Summary:

Female spayed, 10 year-old Chinese Shar-Pei with previous significant medical history including gastric dilatation/volvulus, emergency repair and gastropexy about two and one-half years previously. Chronic IBD was diagnosed, and could not be controlled by conventional therapy before receiving Compound 38. After receiving 7 weeks of 800 mg Compound 38 BID (without conventional IBD treatments), dog #5 was reportedly significantly improved and completely normal.

Dog #5 was treated by local veterinarian with 7 weeks of conventional therapy with Pepcid™, metoclopramide, carafate, diphenoxylate, sulfasalazine, and metronidazole with prescription intestinal diet for IBD (signs: chronic diarrhea w/hematochezia, polyuria/polydypsia, vomiting and flatulence and ultrasound exam revealed mild thickening of intestines). Despite treatment, dog was improved but not clinically normal with owner reporting dog seemed uncomfortable, gassy and occasionally still vomiting. Owner reported that dog became uncomfortable when on conventional therapy when she was due for next dose of medication.

All conventional treatment except prescription bland diet and occasional Pepcid™ was discontinued prior to treatment with Compound 38. Dog reportedly gradually improved over 7 weeks of Compound 38 alone. After 7 weeks of therapy with Compound 38, dog #5 was clinically normal with no signs of IBD.

History and Treatment of Dog #6

Summary:

Female, spayed, 15½ year-old Viszla. Euthanized after 7 weeks of Compound 38 (800-mg, BID) because of signs referable to widespread late stage abdominal neoplastic disease discovered post-mortem.

Contrast radiography about three years earlier was performed after the dog experienced about 8 months of chronic diarrhea. Radiography revealed severe IBD. Dog received various treatments over the next three years that included metronidazole, sulfasalazine, metoclopramide, tylosin, prednisone and hypoallergenic diets which controlled dog's signs when administered chronically.

With exception of diet, conventional treatment was withdrawn prior to treatment with Compound 38. Dog reportedly did very well first 30 days of 800 mg Compound 38 BID; owner reported dog was playful, active and clinically normal ("best she's been in years"). On approximately day 30, dog began with anorexia, vomiting and diarrhea which did not respond to symptomatic and then conventional therapy. Because of her continued deterioration and obvious suffering, owner elected euthanasia and consented to necropsy. Large neoplastic masses were found infiltrating a liver lobe and similar white circular well-circumscribed masses were found throughout liver parenchyma, scattered throughout gastrointestinal tract and in abdominal lymph nodes. A tentative diagnosis of metastatic angiotropic large-cell lymphoma (a very rare cancer) was made.

History and Treatment of Dog #7

Summary:

Female, spayed, 4 year-old Chinese Shar-Pei. Dog #7 had been treated for chronic IBD with conventional therapy of dietary management and tylosin powder for several years.

Tylosin powder was stopped prior to treatment with Compound 38. Dog became anorexic and developed fluid diarrhea. Dog #7 was highly stressed by the office visits and restraint and developed flare-ups of her disease subsequent to similar events in the past. She was treated with Pepto-Bismol only and her diarrhea was worse than when treated more aggressively. After one week on Compound 38, normal stools began to be formed but owner elected to withdraw dog from trial at that time.

Figure 2:
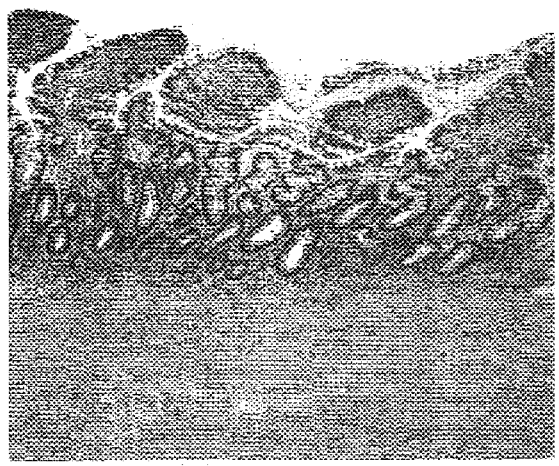
FIG. 2 is a photomicrograph (10× magnification) of a small intestine tissue section taken from the same dog as FIG. 1 after 12 weeks' therapy with a compound employed in the practice of this invention.
Figure 3:
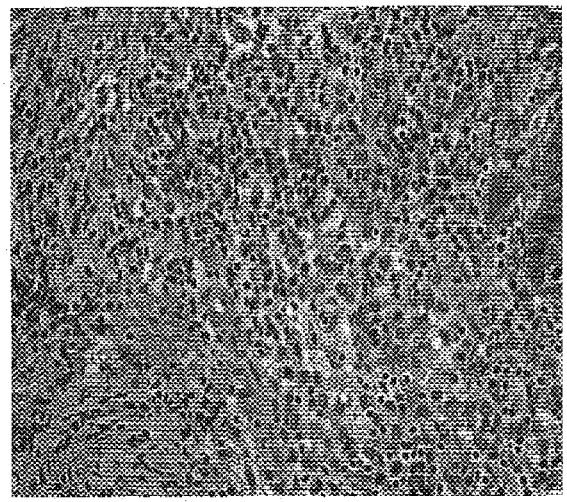
FIG. 3 is a more greatly magnified photomicrograph (40× magnification) of the pre-treatment small intestine tissue section of FIG. 1.
Figure 4:
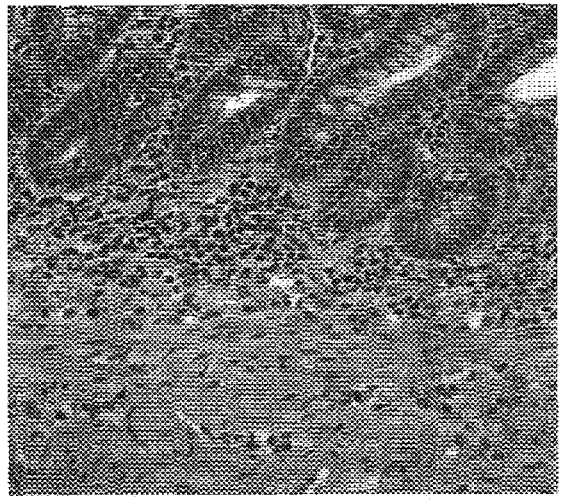
FIG. 4 is a more greatly magnified photomicrograph (40× magnification) of the post-treatment small intestine tissue section of FIG. 2.

The results above were confirmed by histopathology on Dog #1 who had IBD as can be seen by comparing FIGS. 1 and 2. In FIG. 1, small intestinal tissue is shown (10× magnification) from a sample taken before Dog #1 began taking Compound 38. Histopathological interpretation of this section denotes severe IBD characterized by blunt and club-shaped villi with a severe inflammatory cellular infiltrate in the lamina propria. The lamina propria is enlarged. There was no evidence of normal intact epithelial cells at apical surface. Distortion and distension of intestinal crypts along with areas of focal necrosis within crypts. Inflammatory cell types (see FIG. 3, a 40× magnification of the section of FIG. 1) were composed chiefly of lymphocytes, plasma cells, neutrophils and macrophages. In contrast as shown in the photomicrographs presented as FIGS. 2 and 4, the small intestine tissue after 12 weeks of treatment appears remarkably different. The apical surface of the villi (see FIG. 2, a 10× magnification) has intact epithelial and goblet cells. There is minimal to mild inflammatory cells infiltrating the lamina propria (see, FIG. 4, a 40× magnification of the section of FIG. 2) that are primarily composed of lymphocytes, plasma cells and occasionally neutrophils. There are no areas of focal necrosis. As any skilled pathologist should recognize, this section, after treatment, closely mimics normal canine small intestinal tissue.

Figure 5:
FIG. 5 is a slide taken of small intestine tissue taken from a dog with IBD prior to therapy with a compound employed in the practice of this invention where the slide is stained so as to show the presence of PDE2.
Figure 6:
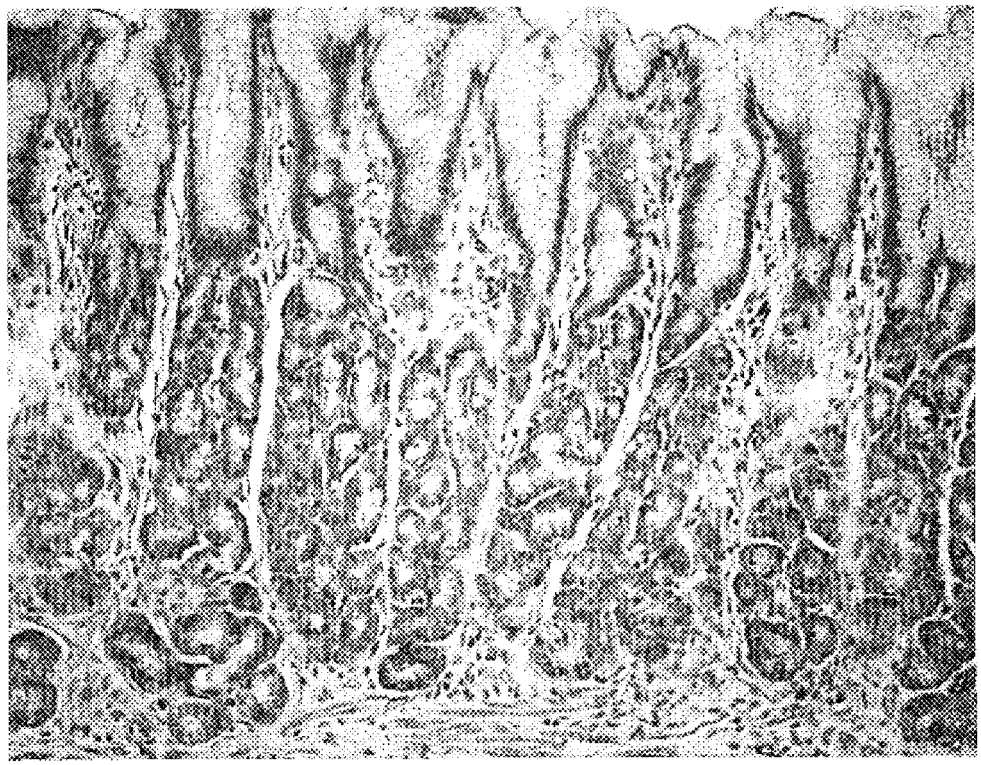
FIG. 6 is a slide taken of small intestine tissue taken from a dog with IBD prior to therapy with a compound employed in the practice of this invention where the slide is stained so as to show the presence of PDE5.

In addition, as shown in FIGS. 5 and 6, the tissue samples from Dog #1 before treatment showed the presence of PDE2 (FIG. 5) and PDE5 (FIG. 6). Specifically, the immunohistostaining of the slide shown in FIG. 5 involved fixing the tissue sample in buffered formalin and embedding it in paraffin. The paraffin-embedded tissue was cut into 4-micron sections, mounted onto polylysine-coated slides, dewaxed in xylene, rehydrated in alcohol and blocked for endogenous peroxidase (0.3% $H_2O_2$ in PBS). The section was treated with blocking serum (PK-4006; VECTOR), and incubated with 1:1000 dilution of PDE 5(1) antibody which was raised against with KLH conjugate of the synthetic peptide TLAFQKEQKLKCECQA. The peptide sequence is from specific region of human PDE2. Immunoreactive complexes were detected using VECTOR elite ABC KIT and visualized with the peroxidase substrate, DAB. Slides were counter stained with hematoxylin. See the brown color in FIG. 5, illustrating the presence of PDE2.

The immunohistostaining of the slide shown in FIG. 6 involved fixing the tissue sample in buffered formalin and embedding it in paraffin. The paraffin-embedded tissue was cut into 4-micron sections, mounted onto polylysine-coated slides, dewaxed in xylene, rehydrated in alcohol and blocked for endogenous peroxidase (0.3% $H_2O_2$ in PBS). The section was treated with blocking serum (PK-4006; VECTOR), and incubated with 1:1000 dilution of PDE 5(1) antibody which was raised against synthetic peptide (CAQLYETSLLENKRNQV) corresponding to the high affinity cGMP binding site of human PDE5. Specificity of the antibody was determined by using control sections that were incubated with blocking peptide (CAQLYETSLLENKRNQV) in the presence of PDE 5(1) antibody, or with preimmune serum. Immunoreactive complexes were detected using VECTOR elite ABC KIT and visualized with the peroxidase substrate, DAB. Slides were counter stained with hematoxylin. See the brown color in FIG. 6, illustrating the presence of PDE5.

It will be understood that various changes and modifications can be made in the details of procedure, formulation and use without departing from the spirit of the invention, especially as defined in the following claims.

We claim:

1. A method of treating inflammatory bowel disease in a mammal with that disease comprising administering to the mammal a pharmacologically effective amount of an inhibitor of both phosphodiesterase 2 and phosphodiesterase 5 with the proviso that said inhibitor has a cyclooxygenase inhibition of less than about 25% at 100 $\mu$M.

2. A method of treating inflammatory bowel disease in a mammal with that disease comprising administering to the mammal a pharmacologically effective amount of an inhibitor of both phosphodiesterase 2 and phosphodiesterase 5 with the proviso that said inhibitor has a cyclooxygenase inhibition of less than about 25% at 100 $\mu$M and an $IC_{50}$ of no more than about 14 $\mu$M for said phosphodiesterases.

* * * * *